US011862341B2

(12) United States Patent
Kim et al.

(10) Patent No.: US 11,862,341 B2
(45) Date of Patent: Jan. 2, 2024

(54) SERVER AND METHOD FOR CLASSIFYING MENTAL STATE

(71) Applicant: HAII Corp., Seoul (KR)

(72) Inventors: Jaejin Kim, Seongnam-si (KR); Chanhyung Kim, Seoul (KR); Seounguk Ha, Seoul (KR); Hoyoung Kim, Seoul (KR); Hunyeop Jeong, Hanam-si (KR); Jeehyun Han, Seoul (KR); Museok Kang, Seoul (KR); Jinhwan Oh, Seoul (KR); Sangho Jin, Incheon (KR); Jeongsang Yoo, Seoul (KR)

(73) Assignee: HAII Corp.

( * ) Notice: Subject to any disclaimer, the term of this patent is extended or adjusted under 35 U.S.C. 154(b) by 0 days.

(21) Appl. No.: 18/081,944

(22) Filed: Dec. 15, 2022

(65) Prior Publication Data
US 2023/0197274 A1    Jun. 22, 2023

(30) Foreign Application Priority Data
Dec. 17, 2021    (KR) ........................ 10-2021-0181749

(51) Int. Cl.
*G16H 50/20*    (2018.01)
*G16H 10/20*    (2018.01)
(Continued)

(52) U.S. Cl.
CPC ............. *G16H 50/20* (2018.01); *G16H 10/20* (2018.01); *G16H 30/20* (2018.01); *G16H 20/70* (2018.01)

(58) Field of Classification Search
CPC ........ G16H 50/20; G16H 10/20; G16H 30/20; G16H 20/70
See application file for complete search history.

(56) References Cited

U.S. PATENT DOCUMENTS

| 11,049,605 B1* | 6/2021 | Peters ..................... G16H 20/70 |
| 2019/0341152 A1* | 11/2019 | Mellem .................. G16H 50/30 |

(Continued)

FOREIGN PATENT DOCUMENTS

| JP | 2018-072876 | 5/2018 |
| KR | 10-2016-0044387 | 4/2016 |

(Continued)

OTHER PUBLICATIONS

Potthoff et al., Effects of Self-Esteem on Self-Viewing: An Eye-Tracking Investigation on Mirror Gazing, Nov. 29, 2021, Behavioral Sciences, pp. 1-10. (Year: 2021).*
Hsieh, The Emotion Recognition System with Heart Rate Variability and Facial Image Features, Jun. 2011, IEEE International Conference on Fuzzy Systems, pp. 1933-1940. (Year: 2011).*

(Continued)

*Primary Examiner* — Christopher L Gilligan
(74) *Attorney, Agent, or Firm* — Pandiscio & Pandiscio

(57) ABSTRACT

A server for classifying a plurality of mental states of a user is provided. The server comprised: a service platform; and a mental state classification platform. The service platform is configured to: provide a questionnaire corresponding to each of the plurality of mental states to a terminal of a user, and receive an answer of the user to the questionnaire from the terminal; receive a face image generated by photographing a face of the user while the user inputs the answer to the questionnaire for each of the plurality of mental states in the terminal of the user; by the terminal, display the face image including at least a middle of a forehead and both cheeks of the face of the user on the user interface so that the user can recognize his/her appearance while inputting the answer to the questionnaire through the user interface of the terminal; and transmit the answer received from the user and the face image to the mental state classification platform.

18 Claims, 16 Drawing Sheets

(51) Int. Cl.
  *G16H 30/20* (2018.01)
  *G16H 20/70* (2018.01)

(56) References Cited

U.S. PATENT DOCUMENTS

| | | | | |
|---|---|---|---|---|
| 2020/0074240 | A1* | 3/2020 | Desai | G06V 40/166 |
| 2022/0192556 | A1* | 6/2022 | Sankar | A61B 5/1118 |
| 2022/0240824 | A1* | 8/2022 | Maier | A61B 5/7267 |
| 2022/0336083 | A1* | 10/2022 | Goldstein | G16H 20/60 |

FOREIGN PATENT DOCUMENTS

| | | | | |
|---|---|---|---|---|
| KR | 10-2111852 | | 5/2020 | |
| KR | 10-2214402 | | 2/2021 | |
| KR | 10-2327669 | | 11/2021 | |
| KR | 10-2021-0028786 | | 2/2022 | |
| WO | WO-2015183930 | A1 * | 12/2015 | A61B 3/112 |
| WO | WO-2020086729 | A1 * | 4/2020 | A61B 5/165 |

OTHER PUBLICATIONS

Forbes M. et al., The Great Recession and Mental Health in the United States, Clinical Psychological Science, vol. 7, No. 5, 2019, pp. 900-913.

Kim D. et al., Trends and Implications of Mental Disorders by Age Group, KIRI, vol. 39, Jan. 2021, pp. 1-8.

Kim J. et al., The Relationship between Autonomous Function and Fatigue Rating in Patients with Fatigue, J Korean Acad Fam Med, vol. 25, No. 1, Jan. 2004, pp. 52-58. (English Abstract).

Kim W. et al., The Impact of Major Depressive Disorder on Productivity in Workers: A Preliminary Study Using WHO-HPQ(Health and Work Performance Questionnaire), J Korean Neuropsychiatr Assoc, vol. 46, No. 6, Nov. 2007, pp. 587-595. (English Abstract).

Tiwari, A. et al., Stress and Anxiety Measurement "In-the-Wild" Using Quality-aware Multi-scale HRV Features, IEEE, 2019, pp. 7056-7059.

Wicklund R. et al., The Effect of Objective Self-Awareness on Predecisional Exposure to Information, Journal of Experimental Social Psychology, vol. 8, Iss. 4, Jul. 1972, pp. 378-387.

* cited by examiner

MAJOR DEPRESSION DISORDER

HR 65.3      76.3      82.3      93.1

ANXIETY DISORDER

LF 5.39      5.51      5.63      5.71

ADJUSTMENT DISORDER

HF 165.42   229.06   296.76   368.89

PTSD

HF 165.42   229.06   296.76   368.89

SUICIDAL IDEATION

HF 5.2      5.5      6.3      6.9

INSOMNIA

LF 6.94      6.62      7.11      8.14

SERVER AND METHOD FOR CLASSIFYING MENTAL STATE

REFERENCE TO PENDING PRIOR PATENT APPLICATION

This patent application claims benefit of Korean Patent Application No. 10-2021-0181749, filed Dec. 17, 2021, which patent application is hereby incorporated herein by reference.

FIELD OF THE INVENTION

The present disclosure relates to a mental state classification server and a mental state classification method, specifically, a mental state classification server that provides a classification service of at least one mental state to a user, a terminal used therefor, a method for classifying a mental state, and a method for providing a mental state classification service.

BACKGROUND OF THE INVENTION

Over the past ten years, a number and cost of treatment for mental disorders has steadily increased, and a lifetime prevalence of seventeen mental disorders is 25.4%, indicating that one in four adults has experienced at least one mental disorder in their lifetime (KIRI, Trends and Implications of Mental Disorders by Age Group, Volume: No. 39, Jan. 26, 2021). In addition, according to the same survey, the number of psychiatric treatments related to youth and women has steadily increased over the past five years, which is attributed to the high stress and low socioeconomic level of the corresponding generation. Therefore, in consideration of social cost of mental illness, prevention, early detection, and early treatment are of utmost importance.

Moreover, as COVID-19 epidemic is prolonged, the increase in the number of psychiatric patients is accelerating, and one of the causes, 'anxiety about a rapid economic recession and a surge in the unemployment rate', can be considered to have been caused by employment shock after COVID-19 incident. In this regard, according to a study by Forbes, M. K., & Krueger, R. F. (The Great Recession and mental health in the United States. Clinical Psychological Science, 7(5), 900-913.), depression and anxiety increased in many countries during a financial crisis, and rising income inequality due to rising unemployment adversely affects life expectancy and suicide rate.

On the other hand, according to the research paper (*J Korean Neuropsychiatr Assoc*/Volume 46, No 6/November, 2007), workers with major depression had more days of absenteeism and more early leave than workers without major depression, and workers with major depression were rated much lower in the evaluation of their job performance. In other words, it was suggested that the overall job performance was greatly deteriorated due to major depression. From this, it can be seen that emotional problems of workers have a great influence on productive capacity of workers.

Therefore, it is necessary to check and manage mental health of workers in order to increase productivity of a company. Moreover, it can be seen that its importance is growing in the midst of social difficulties caused by the recent pandemic of COVID-19.

On the other hand, in the prior art, in order to understand the mental state of the worker, a user wrote an answer to a questionnaire provided by a clinical expert, and the clinical expert directly classified the mental state of the user based on the answer written in the questionnaire.

However, since workers do not want to disclose their current mental state to an outside world or tend to reduce seriousness of the state, in many cases, workers were unable to answer honestly enough to express their actual mental state. Moreover, there is a high probability that workers cannot objectively recognize their own mental state, so there is a great limit to classifying the mental state of workers by filling out the questionnaire.

However, there is still no non-face-to-face service for early classification of mental health status by individuals or companies. Accordingly, there is an urgent need for research and development for this purpose.

PRIOR DISCLOSURES (Patent Document 1) Korean Patent Registration No. 10-2111852

An object of the present disclosure is to provide a new method capable of providing accurate and highly reliable mental state classification service to a user in a non-face-to-face manner by providing a mental state classification server, a terminal used therefor, a mental state classification method, and a method for providing a mental state classification service.

SUMMARY OF THE INVENTION

According to one aspect of the present disclosure, a server for classifying a plurality of mental states of a user is provided. The server comprises: a service platform and a mental state classification platform, wherein the service platform is configured to: provide a questionnaire corresponding to each of the plurality of mental states to a terminal of a user, and receive an answer of the user to the questionnaire from the terminal; receive a face image generated by photographing a face of the user while the user inputs the answer to the questionnaire for each of the plurality of mental states in the terminal of the user; enable the terminal to display the face image including at least a middle of a forehead and both cheeks of the face of the user on the user interface so that the user can recognize his/her appearance while inputting the answer to the questionnaire through the user interface of the terminal; and transmit the answer received from the user and the face image to the mental state classification platform, wherein the mental state classification platform is configured to: execute a first algorithm to obtain a first numerical value indicating a possibility that the user corresponds to each of the plurality of mental states based on the answer received from the terminal, extract heart rate variability (HRV) data of the user based on the face image received from the terminal; execute a second algorithm to obtain a second numerical value indicating a possibility that the user corresponds to each of the plurality of mental states based on the extracted HRV data; execute a third algorithm to obtain a third numerical value indicating a possibility that the user corresponds to each of the plurality of mental states based on the first numerical value and the second numerical value; and generate a mental state classification result report indicating the third numerical value, wherein each of the first numerical value and the second numerical value includes a severity of the mental state of the user, and wherein the third algorithm is configured to set a weight to be reflected in the third numerical value to each of the first numerical value and the second numerical value and obtain the third numerical value indicating a final mental state classification result from the first numerical value and the second numerical value based on the weight.

According to one embodiment of the present disclosure, wherein the plurality of mental states are at least two of major depressive disorder, anxiety disorder, adjustment disorder, post-traumatic stress disorder (PTSD), suicidal ideation, and insomnia.

According to one embodiment of the present disclosure, the mental state classification platform is configured to receive the face image from the terminal in real time and extract the HRV data of the user in real time.

According to one embodiment of the present disclosure, the service platform is configured to provide a questionnaire for each of the plurality of mental states to the user, and receive in real time the face image for each questionnaire section, which is generated by photographing the face image of the user for each questionnaire section for each of the plurality of mental states, and wherein the mental state classification platform is configured to obtain the third numerical value for each of the plurality of mental states based on the first numerical value based on the answer to the questionnaire for each of the plurality of mental states and the second numerical value based on the entire face image generated for each questionnaire section of each of the plurality of mental states.

According to one embodiment of the present disclosure, the service platform is configured to receive the mental state classification result report from the mental state classification platform and provide the mental state classification result report to the user.

According to one embodiment of the present disclosure, the mental state classification result report further comprises a behavioral recommendation for the mental state, in response to the third value for each of the plurality of mental states being greater than or equal to a selected first scale.

According to one embodiment of the present disclosure, the mental state classification server is configured to perform classification of each of the plurality of mental states of a plurality of users included in a specific group, and wherein the mental state classification platform is configured to further generate the mental state classification result report of the specific group including an average of the third numerical value of each of the plurality of users derived from the third algorithm and not including the third numerical value of each of the users, and wherein the service platform is configured to receive the mental state classification result report of the specific group from the mental state classification platform, and provide the received mental state classification result report of the specific group to an administrator who manages a plurality of users.

According to one embodiment of the present disclosure, the mental state classification platform is configured to: receive a result of classifying the plurality of mental states of the user by a person; derive a fourth algorithm that improves the third algorithm by performing machine learning of artificial intelligence based on the first numerical value, the second numerical value, the third numerical value, and the result classified by the person; and replace the third algorithm with the derived fourth algorithm.

According to another aspect of the present disclosure, a terminal configured to be accessible to a service platform provided in a mental state classification server, comprising a user interface; a camera; a wireless communication unit; and a processor is provided, wherein the user interface is configured to display a questionnaire for each classification of a plurality of mental states provided from the service platform and to allow a user of the terminal to input an answer to the questionnaire, wherein the camera is configured to generate a face image by photographing a face of the user of the terminal while inputting the answer to a questionnaire for classifying each of the plurality of mental states, wherein the wireless communication unit is configured to receive the questionnaire from the service platform, or to transmit the answer to the questionnaire input through the user interface and the generated face image to the service platform, and wherein the processor is configured to: when providing the questionnaire to the user through the user interface, control the user interface to transmit the questionnaire to the user in a form of a chatting message; control the camera to generate the face image by photographing the face of the user while the user inputs the answer to the questionnaire through the user interface; control the wireless communication unit to transmit the generated face image of the user to the service platform; and display the face image including at least a middle of a forehead and both cheeks of face of the user on the user interface so that the user can recognize his/her appearance while inputting the answer to the questionnaire through the user interface.

According to one embodiment of the present disclosure, the processor is configured to: classify each of the plurality of mental states of the user, and control the user interface to provide a next questionnaire after providing one questionnaire to the user interface; photograph the face of the user with the camera for each section in which the user inputs the answer to a questionnaire corresponding to each of the plurality of mental states; control the wireless communication unit to transmit the face image generated through the camera to the service platform.

According to another aspect of the present disclosure, a method of classifying a plurality of mental states of a user of a terminal using a mental state classification server including a service platform and a mental state classification platform is provided. The method comprises: by the service platform, providing a questionnaire related to each of the plurality of mental states to the user through the terminal to classify the plurality of mental states; by the service platform, receiving an answer input by the user to the questionnaire and storing the received answer; by the service platform, receiving a face image generated by photographing a face of the user while conducting the questionnaire for each of the plurality of mental states and the user's inputting the answer corresponding to each of the plurality of mental states into the terminal, and transmitting the received face image to the mental state classification platform; by the mental state classification platform, obtaining a first value indicating a possibility that the user corresponds to each of the plurality of mental states based on the received answer by executing a first algorithm; by the mental state classification platform, extracting heart rate variability (HRV) data of the user based on the transmitted face image; by the mental state classification platform, obtaining a second value indicating a possibility that the user corresponds to each of the plurality of mental states based on the extracted HRV data of the user by executing a second algorithm; by the mental state classification platform, executing a third algorithm, and obtaining a third numerical value indicating a possibility that the user corresponds to each of the plurality of mental states based on the first numerical value and the second numerical value; by the mental state classification platform, generating a mental state classification result report indicating the third numerical value of each of the plurality of mental states, and transmitting the generated mental state classification result report to the service platform; and by the service platform, providing the mental state classification result report to the user, wherein the terminal is configured to display a face image including at least a middle of a forehead and both cheeks of the face of the user on a user interface so that the user can recognize his/her appearance while inputting the answer to the questionnaire through the user interface of the terminal, wherein each of the first numerical value and the second numerical value includes a severity of the mental state of the user, and wherein the third algorithm is configured to set a weight to be reflected in the third numerical value to each of the first numerical value and the second numerical value and obtain the third numerical value indicating a final mental state classification result from the first numerical value and the second numerical value based on the weight.

According to one embodiment of the present disclosure, the method comprises classifying each of the plurality of mental states of a plurality of users, and further comprising: by the mental state classification platform, generating a group's mental state classification result report indicating an average of the third numerical value of each of the plurality of users derived from the third algorithm; and by the service platform, receiving the group's mental state classification result report from the mental state classification platform, and providing the received mental state classification result report to an administrator who manages the plurality of users.

According to one embodiment of the present disclosure, the generating a mental state classification result report indicating the third numerical value comprising: in response to the mental state classification platform determining that the third numerical value is greater than or equal to a reference value, adding an action recommendation for the mental state having the third numerical value.

According to one embodiment of the present disclosure, the method further comprises: by the mental state classification platform, receiving a result of classifying the plurality of mental states of the user by a person; by the mental state classification platform, deriving a fourth algorithm that improves the third algorithm by performing machine learning of artificial intelligence based on the first numerical value, the second numerical value, the third numerical value, and the result classified by the person; and by the mental state classification platform, replacing the third algorithm with the derived fourth algorithm.

According to another aspect of the present disclosure, a method of providing a classification service of a plurality of mental states to a user using a mental state classification server including a service platform and a mental state classification platform is provided, which comprises: by the service platform, receiving an application for a mental state classification service from at least one of the user and an administrator who manages users; by the service platform, receiving personal information of the user and storing the personal information; by the service platform, notifying completion of registration of mental state classification service to at least one of the user and the administrator of the user; by the service platform, providing a questionnaire for classification of each of the plurality of mental states to a terminal of the user; by the service platform, receiving an answer of the user to the questionnaire from the terminal and storing the received answer; by the service platform, receiving a face image generated by photographing a face of the user while conducting the questionnaire for each of the plurality of mental states and the user's inputting the answer corresponding to each of the plurality of mental states into the terminal; by the service platform, transmitting the answer of the user to the questionnaire and the received face image to the mental state classification platform, and requesting the mental state classification platform to classify each of the plurality of mental states based on the transmitted answer of the user and perform HRV analysis based on the transmitted face image; by the mental state classification platform, extracting HRV data of the user based on the face image; by the mental state classification platform, classifying a possibility of corresponding to each of the plurality of mental states based on the answer to the questionnaire and the extracted HRV data, and generating a mental state classification result report based on classified results; by the mental state classification platform, transmitting the mental state classification result report to the service platform; and by the service platform, providing the mental state classification result report to the user, wherein the receiving a face image generated by photographing a face of the user comprising: displaying a face image including at least a middle of a forehead and both cheeks of the face of the user on a user interface of the terminal so that the user can recognize his/her appearance while inputting the answer to the questionnaire through the user interface.

According to one embodiment of the present disclosure, the receiving a face image generated by photographing a face of the user comprises: by the service platform, receiving a face image generated by photographing a face for each section in which the user inputs the answer to a questionnaire for each of the plurality of mental states, and transmitting the face image to the mental state classification platform, and wherein the extracting HRV data of the user comprising: by the mental state classification platform, extracting HRV data of the user corresponding to each of the plurality of mental states based on each face image generated for each questionnaire section for each of the plurality of mental states.

According to one embodiment of the present disclosure, the method comprises classifying each of the plurality of mental states of a plurality of users, and further comprising: by the mental state classification platform, further generating a group's mental state classification result report of indicating an average of possibilities corresponding to each of the plurality of mental states of the plurality of users; and by the service platform, receiving the group's mental state classification result report from the mental state classification platform, and providing the received group's mental state classification result report to an administrator who manages the plurality of users.

According to one embodiment of the present disclosure, the providing a questionnaire for classification of each of the plurality of mental states to a terminal comprises: transmitting the questionnaire to the user in a form of a chatting message by a virtual person in the user interface of the terminal.

According to one embodiment of the present disclosure, after the providing the mental state classification result report to the user, the method further comprises: by the service platform, receiving the face image of the user regularly photographed for a predetermined period, and transmitting the received face image to the mental state classification platform; by the mental state classification platform, extracting HRV data based on the user's face image; by the mental state classification platform, generating a mental state classification result report indicating a possibility of corresponding to each of the plurality of mental states based on the extracted HRV data; and by the service platform, providing the mental state classification result report to the user.

According to an embodiment of the present disclosure, the mental state classification server of the present disclosure includes a service platform and a mental state classification platform, so that the psychological state of the user can be finally classified by considering both the result of classifying the mental state based on the answer to the questionnaire for classifying the mental state and the result of classifying the mental state based on the HRV data. Accordingly, the mental state classification server of the present disclosure can effectively increase accuracy and reliability of the user's mental state classification.

Furthermore, the mental state classification server of the present disclosure extracts HRV data based on the user's answer to the questionnaire and the face image of the terminal user captured by the camera while the user inputs the answer into the terminal, so that it is possible to solve the problem of the prior art that occurs when the user does not answer accurately enough to represent his/her actual mental state. That is, even if the user does not input an honest answer to the questionnaire corresponding to any one of the mental states, the mental state classification server of the present disclosure may analyze a more accurate mental state classification for a corresponding mental state through the face image captured while inputting the answer to the questionnaire.

DESCRIPTION OF THE INVENTION

Figure 1:
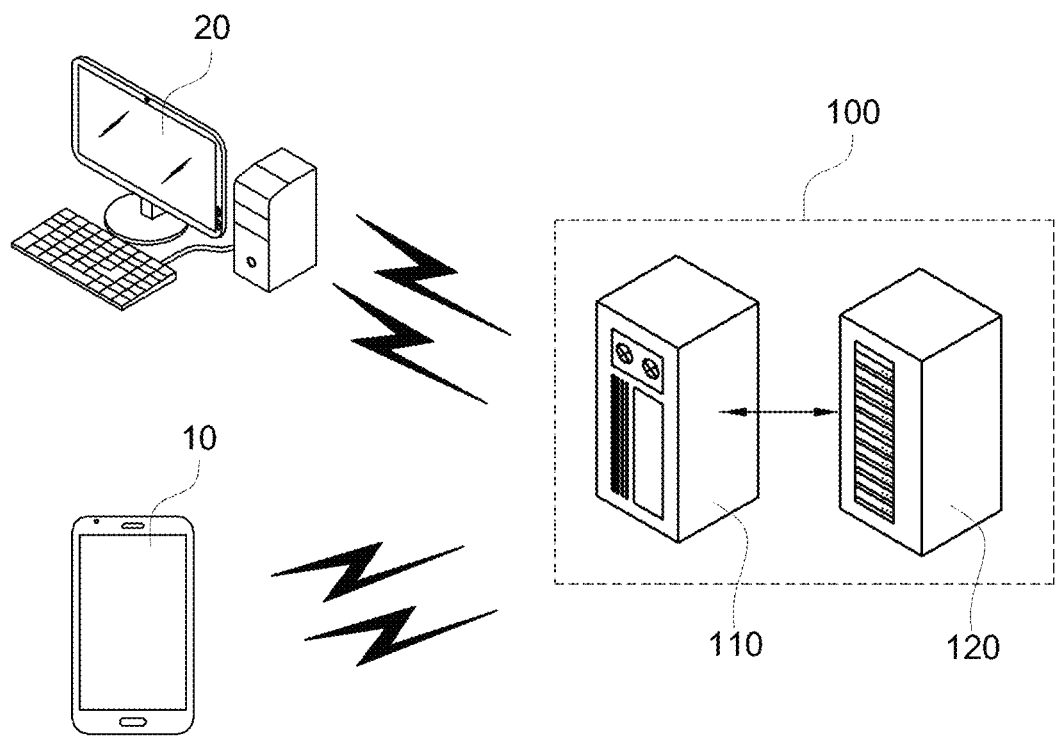
FIG. 1 is a diagram illustrating a configuration of a mental state classification server according to an embodiment of the present disclosure.

Hereinafter, with reference to the accompanying drawings, the embodiments of the present disclosure will be described in detail so that those of ordinary skill in the art to which the present disclosure pertains can readily implement them. However, the present disclosure may be implemented in several different forms and is not limited to the embodiments described herein.

In order to clearly explain the present disclosure in the drawings, parts irrelevant to the description are omitted, and similar reference numerals are attached to similar parts throughout the specification.

Throughout the specification, when a part "includes" or "comprises" a certain component, it means that other components may be further included, rather than excluding other components, unless otherwise stated.

It is to be understood that the techniques described in the present disclosure are not intended to be limited to specific embodiments, and include various modifications, equivalents, and/or alternatives of the embodiments of the present disclosure.

The expression "configured to (or set to)" as used in this disclosure, depending on the context, can be used interchangeably with, for example, "suitable for", "having the capacity to," "designed to", "adapted to", "made to", or "capable of". The term "configured (or configured to)" is not necessarily means only "specifically designed to" hardware. Instead, in some circumstances, the expression "a device configured to" means that the device is "capable of" with other devices or components. For example, the phrases "a processor configured (or configured to perform) A, B, and C," "a module configured (or configured to perform) A, B, and C", means a dedicated processor (for example, it may mean an embedded processor) or a generic-purpose processor (e.g., a CPU or an application processor) capable of performing corresponding operations by executing one or more software programs stored in a memory device.

Hereinafter, an embodiment of the present disclosure will be described with reference to the attached drawings.

Figure 2:
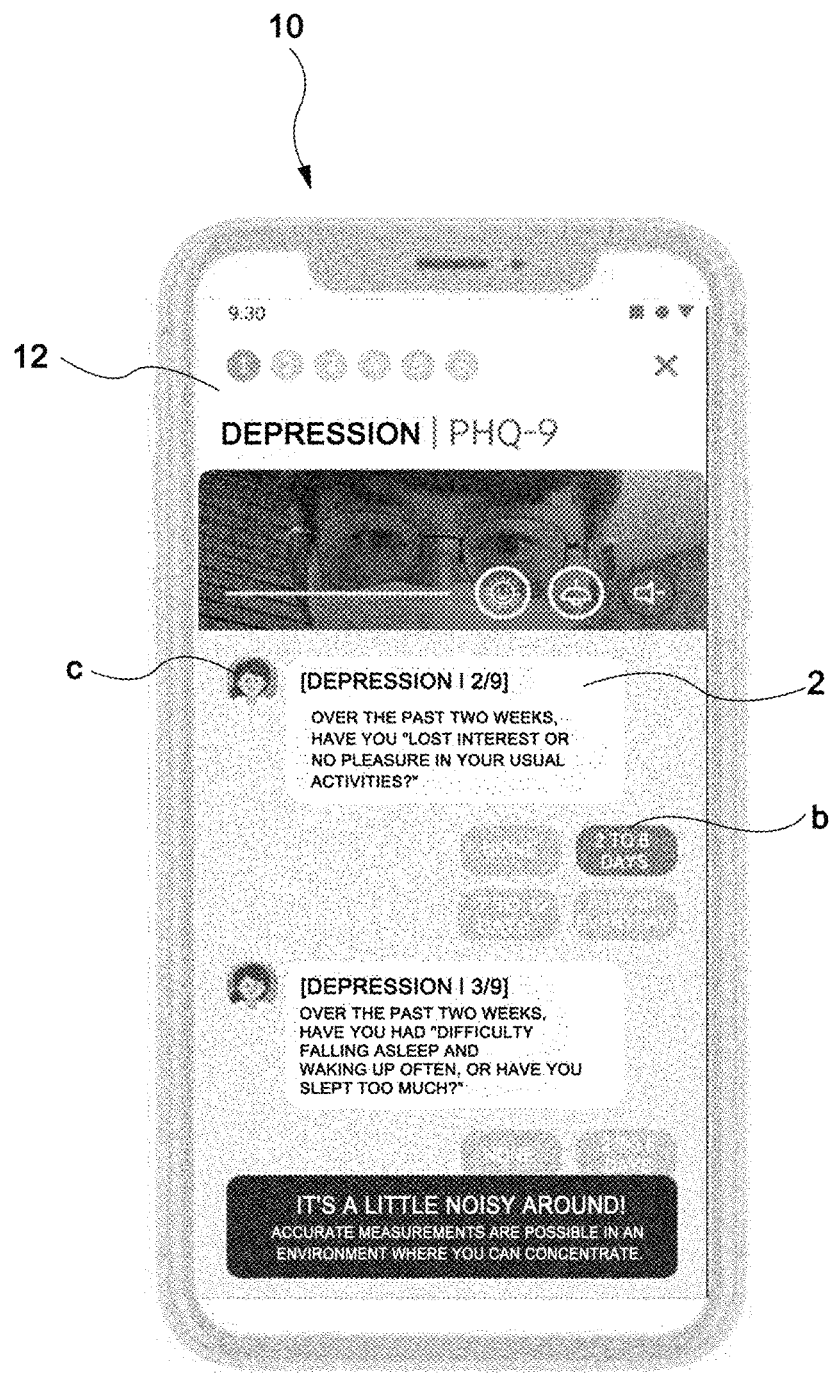
FIG. 2 is a schematic diagram illustrating a state of a receiving terminal provided with a questionnaire of a mental state classification service through a mental state classification server according to an embodiment of the present disclosure.

FIG. 1 is a diagram illustrating a configuration of a mental state classification server 100 according to an embodiment of the present disclosure; and FIG. 2 is a schematic diagram illustrating a state of a receiving terminal 10 provided with a questionnaire of a mental state classification service through a mental state classification server 100 according to an embodiment of the present disclosure.

Referring to FIG. 1 and FIG. 2, the mental state classification server 100 according to an embodiment of the present disclosure includes a service platform 110 and a mental state classification platform 120. The service platform 110 and the mental state classification platform 120 include a computing system, hardware on which a program is executed, software running on the hardware, and a cloud service, and may be connected to each other or other servers through a network. In addition, the service platform 110 and the mental state classification platform 120 include a system configured to provide a service at the request of a user or administrator; and provide a distributed processing form that operates one or more application programs in a mutually cooperative environment. The service platform 110 and the mental state classification platform 120 may include hardware such as a processor, a storage or database, and a communication module.

Specifically, the service platform 110 may provide a questionnaire for classification of at least one mental state to a user's terminal 10. Here, the at least one mental state may include major depression disorder, anxiety disorder, adjustment disorder, PTSD, suicidal ideation, and insomnia. Accordingly, the questionnaire provided by the service platform 110 includes a questionnaire related to at least one of major depressive disorder, anxiety disorder, adjustment disorder, PTSD, suicidal ideation, and insomnia.

For example, clinical scales of mental states that can be used in the questionnaire are shown in Table 1 below.

TABLE 1

| Category | Name of mental state | Clinical questionnaire tool |
|---|---|---|
| 1 | major depressive disorder | PHQ-9 (Patient Health Questionnaire 9) |
| 2 | anxiety disorder | GAD-7 (Generalized Anxiety Disorder 7) |
| 3 | adaptation disorder | ADNM-4 (Adjustment Disorder-New Module-4) |
| 4 | post-traumatic stress disorder | K-PC-PTSD-5 (Korean version of the Primary Care PTSD Screen for DSM-5) |
| 5 | suicide accident | P4 (P4 Suicidality Screener) |
| 6 | insomnia | ISI (Insomnia Severity Index) |

For example, the service platform 110 may provide a questionnaire for classification of at least one mental state through an installed application program (e.g., an app) of the terminal 10. For example, as shown in FIG. 2, when the service platform 110 provides the questionnaire to the user's terminal 10, a virtual person c transmits the questionnaire in a form of a chatting message 2 to the user. In one embodiment, the questionnaire may be provided at the same time as notifying the user of what kind of mental state the questionnaire is, how many questions the questionnaire are comprised of, and the conditions that the user should consider when answering the questionnaire. For example, a plurality of questionnaires may be performed for each category.

However, the present disclosure is not necessarily limited to this form, and the mental state classification server of the present disclosure may be provided without notifying the user of which mental state the questionnaire is related to. For example, the service platform 110 may provide a questionnaire regarding the mental state of major depressive disorder; and may proceed with the questionnaire without informing that the questionnaire provided to the user has a purpose of examining major depressive disorder.

In addition, the service platform 110 may receive the user's personal information from the terminal 10 and store it. To this end, the service platform 110 may include a database (not shown) to store the personal information. However, the present invention is not limited thereto, and the service platform 110 may transmit the user's personal information to an external server (e.g., a cloud server) to store the user's personal information. In this case, the personal information may be stored in a storage space of an external server accessible to the service platform 110. Here, the 'personal information' may be biographical information of the user. For example, the personal information may be at least one of real name, gender, age (date of birth), phone number, and workplace information (company name, affiliated department, affiliated team, job responsibility, position, and number of years of employment).

Figure 3:
FIG. 3 shows classification criteria graphs for classifying a plurality of mental states through HRV data of a mental state classification server according to an embodiment of the present disclosure.
Figure 3:
Figure 3:
Figure 3:
Figure 3:
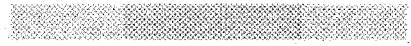
Figure 3:
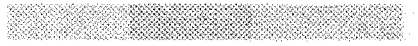

Furthermore, the service platform 110 may receive the user's answer to the questionnaire for classification of at least one or more mental states and transmit it to the mental state classification platform 120. At this time, the service platform 110 may store the answer to the questionnaire input by the user through the user interface 12 of the terminal 10. For example, the user may input the answer to the questionnaire through a touch input using a display of the terminal, a microphone (i.e., voice input), a keyboard, and a keyboard application. Alternatively, for example, as shown in FIG. 3, the user may input the answer by clicking a button b corresponding to the answer of the questionnaire displayed on the user interface 12.

In addition, the service platform 110 can be configured to conduct a questionnaire on the mental state in the terminal 10; use the camera of the terminal 10 to capture a face image of the user while the user inputs the answer; receive the image in real time; and transmit the received face image to the mental state classification platform 120. That is, the mental state classification platform 120 may receive the face image from the terminal in real time and extract heart rate variability (HRV) data of the user in real time. For example, the service platform 110 may provide the user with questionnaires corresponding to a plurality of mental states to the terminal 10; and receive, in real time, the face image generated by photographing a user's face while the user inputs answers to the questionnaires.

At this time, the service platform 110 may provide the user with a questionnaire about a plurality of mental states; receive the face image generated by photographing the user's face image in real time while inputting the answer to the questionnaire for each of the plurality of psychological states; transmit the received face image to the mental state classification platform 120.

In addition, the mental state classification platform 120 may be configured to obtain a third value for each of the plurality of mental states, based on a first numerical value based on the answer to the questionnaire for each of the plurality of mental states and a second numerical value based on the face image generated while inputting the answer.

For example, while the user inputs the answer to a questionnaire corresponding to the mental state, a minimum time for photographing an image by the camera 14 may be determined by the service provider of the service platform 110. For example, the minimum time for photographing an image of the camera 14 may be preferably 3 to 5 minutes. However, the present invention is not limited thereto, and the photographing time may be shorter, such as within 1 minute, 2 minutes, or 3 minutes, or longer than the minimum time range. For example, in response to receiving the user's application for mental state classification for major depressive disorder and anxiety disorder, the service platform 110 may transmit questionnaires about major depressive disorder and anxiety disorder to the terminal 10 of the user and receive, in real time, the face image captured while the user inputs answers to the questionnaires into the terminal 10. In addition, the mental state classification platform 120 may receive the face image from the service platform 110 and extract HRV data based on the received face image. HRV may be measured using the face image generated while a plurality of questionnaires is performed for each category. In this case, the measurement of HRV may be performed in real time.

Therefore, in the embodiment of the present disclosure, since the classification of the mental state is performed by extracting HRV data based on the image of the user's face together with the answer to the questionnaire for classification of the mental state, the embodiment of the present disclosure is capable of more accurate mental state classification than a classification of mental states by conducting only simple questionnaires or simply analyzing HRV data.

In more detail, the at least one mental state may be at least one of major depression disorder, anxiety disorder, adjustment disorder, PTSD, suicidal ideation, and insomnia.

In another embodiment of the present disclosure, the mental state classification server 100 may perform classification of a plurality of mental states; and the service platform 110 may provide the terminal 10 with a plurality of questionnaires for classifying each of a plurality of mental states to the user. Unlike the above-described embodiment, the service platform 110 may receive a user's face image from the terminal 10 for each section in which the service platform 110 provides a questionnaire for each of a plurality of mental states and receives an answer. For example, the plurality of mental states received by the service platform 110 may be major depressive disorder, anxiety disorder, adaptation disorder, PTSD, insomnia, and suicidal ideation. In response to this, the service platform 110 may sequentially provide questionnaire(s) corresponding to each of the depression, anxiety disorder, and adaptation disorder to the terminal 10. In addition, while each time the user inputs the answer to each of the questionnaires provided sequentially in this way, the service platform 110 may control the camera 14 of the terminal 10 to photograph the user's face and generate the face image corresponding to each of questionnaires of the plurality of psychological state for a predetermined time (e.g., 1 minute, 2 minutes, 3 minutes, 5 minutes, etc.).

For example, the service platform 110 may provide the user with a questionnaire related to major depressive disorder through the terminal 10 and receive a face image of a first section in which the user inputs the answer into the terminal 10; provide the user with a questionnaire related to anxiety disorder and receive a face image of a second section in which the user inputs the answer into the terminal 10; provide the user with a questionnaire related to adjustment disorder and receive a face image of a third section in which the user inputs the answer into the terminal 10; provide a questionnaire related to PTSD to the user and receive a face image of a fourth section in which the user inputs the answer into the terminal 10; provide the user with a questionnaire related to insomnia and receive a face image of a fifth section in which the user inputs the answer into the terminal 10; and provide the user with a questionnaire related to suicidal ideation and receive a face image of a sixth section in which the user inputs the answer into the terminal 10. Thereafter, the mental state classification platform 120 may extract each HRV data by using, in real time, the face image obtained for each section in the first section to the sixth section.

In one embodiment, the service platform 110, in response to the fact that the face image received from the terminal 10 does not meet the criterion (level) for extracting accurate HRV data, may capture the user' face again for the remaining time even after all questionnaires have been completed and extract HRV data. For example, for this purpose, a virtual agent may provide feedback on the service to the user or provide a brief questionnaire to additionally extract HRV data after image capturing for all provided questionnaires is finished, and additionally perform image capturing of the camera 14 while the user inputs answers to a brief questionnaire. For example, in response to determining that the face image captured in the sixth section does not meet the standard (level) for extracting accurate HRV data, the service platform 110 may request re-measurement through the terminal 10. The service platform 110 may provide a brief questionnaire to the terminal 10 in response to the user's response to the re-measurement; and store the face image of a seventh section captured while the user inputs the answer.

At this time, the terminal 10 may allow the virtual person (agent) displayed on the user interface 12 to interact with the user by transmitting a brief questionnaire about the psychological state (e.g., suicidal ideation) to be measured in the sixth section to the user.

Based on the provision of a questionnaire on each psychological state and the face image generated for each questionnaire section on each mental state received from the terminal 10 (for example, the face image of each of the first to sixth sections), the mental state classification platform 120 may extract HRV data, evaluate the plurality of psychological states based on the extracted HRV data, and classifies the psychological state in which the user is placed.

The mental state classification platform 120 may be configured to obtain a third value for each of the plurality of mental states, based on a first numerical value based on the answer to the questionnaire for each of the plurality of mental states and a second numerical value based on the face image generated while inputting the answer.

Therefore, the mental state classification server 100 of the present disclosure has an advantage of being able to analyze a more accurate mental state classification for a corresponding mental state through a face image captured while inputting the answer to a questionnaire corresponding to the mental state, even if the user does not input an honest answer to a questionnaire for classifying a plurality of mental states.

The face image may be generated by photographing the user's face using the camera 14 provided in the terminal 10. In addition, the service platform 110 may receive camera photographing time information of the user and transmit it to the mental state classification platform 120.

The mental state classification platform 120 may execute a first algorithm. The mental state classification platform 120 may be configured to execute the first algorithm to obtain a first numerical value indicating a possibility that the user corresponds to the mental state based on the answer received from the terminal 10. The first numerical value may include a scale indicating a severity of the user's mental health state. In one embodiment, the severity may be expressed as a percentage or a range of scores. The severity of the psychological health state may be expressed by classifying a scale into, for example, mild, moderate, and severe. Alternatively, the severity of the psychological health state may be expressed by classifying a scale into five levels of, for example, no disability, mild, moderate, moderately severe, and severe. This stage division is exemplary, and the steps can be variously modified by setting.

Also, the mental state classification platform 120 may extract HRV data based on the user's face image stored in the service platform 110. Here, the HRV refers to a degree of variability in the heart rate. That is, the HRV refers to a minute variability between one cardiac cycle and the next. The heart rate is determined by an influence of the autonomic nervous system on the intrinsic spontaneity of the sinus node; and is related to an interaction between sympathetic and parasympathetic nerves. This interaction changes moment by moment according to changes in an internal/external environment, resulting in a change in heart rate.

In addition, the method of extracting HRV data based on the user's face image may include a method of predicting a heart reaction by analyzing the color change of the face over time from the face image photographed with the camera 14.

Furthermore, in the method of extracting HRV data based on the user's face image, the face image received by the mental state classification platform 120 may be image-processed in real time to extract HRV data. For example, the method of extracting the HRV data may include steps of: by the mental state classification platform 120, receiving a face image from the terminal 10 in real time, and detecting the user's face in a frame of the received face image; in response to the face not being detected in the frame, re-detecting the user's face; defining a measurement area in the detected face; extracting a color-based fine movement signal by tracking the head movement due to a fine movement and extracting a fine change in color accordingly; converting the extracted facial fine movement signal into a frequency band through the fast Fourier transform (FFT) to extract a power spectrum and normalizing it to extract relative frequencies; comparing similarity between the relative frequencies of the facial fine movement signal extracted from the face image and the built rule base to select K heartbeat candidates; recognizing an average heart rate of K heart rate candidates extracted from the rule base based on the K-nearest neighbor algorithm through similarity comparison as a final heart rate; and extracting the HRV variables (HRV data) by calculating formulas of the HRV variables from the final recognized heart rate. Examples of the HRV variables are shown in Table 2 below. In the step of extracting the color-based fine movement, each fine movement signal may be normalized to remove noise other than the heartbeat component, and a bandpass filter may be applied to the heartbeat band.

TABLE 2

<Descriptions of the HRV variables>

| No. | Domain | HRV variable | Explanation |
|---|---|---|---|
| 1 | Time Domain | HR | Average heart rate per minute (bpm) |
| 2 | | SDNN | Standard deviation of intervals between all peaks |
| 3 | | RMSSD | Square root of the mean of the sum of the squares of the differences between adjacent peaks |
| 4 | | pNN50 | Proportion (%) of difference between adjacent peaks greater than 50 msec. |
| 5 | Frequency Domain | VLF | Power values in the 0.0033 to 0.04 Hz band in the frequency domain |
| 6 | | LF | Power values in the 0.04 to 0.15 Hz band in the frequency domain |
| 7 | | HF | Power values in the 0.15-0.4Hz band in the frequency domain |
| 8 | | VLF (%) | VLF divided by the total power value (power value in the 0.0033~0.4 Hz band) |
| 9 | | LF (%) | LF divided by total power value (power value in 0.0033~0.4 Hz band) |
| 10 | | HF (%) | HF divided by the total power value (power value in the 0.0033~0.4 Hz band) |
| 11 | | lnVLF | VLF taken as natural logarithm |
| 12 | | lnLF | LF taken as natural logarithm |
| 13 | | lnHF | HF taken natural logarithm |
| 14 | | LF/HF | LF divided by HF |

TABLE 2-continued

<Descriptions of the HRV variables>

| No. | Domain | HRV variable | Explanation |
|---|---|---|---|
| 15 | | VLF/HF | VLF divided by HF |
| 16 | | Total Power | Power spectrum band between 0.0033 and 0.4 Hz |
| 17 | | Dominant Power | The power value of the highest peak in the power spectrum |
| 18 | | Dominant Hz | Frequency value (Hz) of the highest peak in the power spectrum |
| 19 | | Peak power | Power spectrum band from −0.015 Hz to +0.015 Hz centered at peak Hz |
| 20 | | Peak Hz | Frequency value (Hz) of the highest peak in the power spectrum band between 0.04 and 0.26 Hz |
| 21 | | Coherence ratio | Peak Power divided by the difference between Total Power and Peak Power |

Such HRV may be used to classify human mental states. In order to classify such a mental state, the mental state classification platform 120 of the mental state classification server 100 of the present disclosure may use a clinical surrogate marker. Here, the clinical surrogate marker refers to an indirect indicator of a disease state or treatment; and refers to laboratory measurements or physical signs used to substitute actual clinically meaningful outcome variables (i.e., clinical endpoints).

In this regard, according to Kisam Jung (Kisam Jung. (2004). Overview of HRV. Korean Journal of Family Medicine, 25(1), 52-58.), autonomic nervous system dysfunction is associated with many clinical diseases and symptoms such as depression, anxiety, and insomnia; and HRV analysis is a non-invasive and reliable test method that can measure autonomic nervous system function and can be widely applied to various diseases and conditions related to autonomic nervous system.

Also, a research paper (Tiwari, A., Narayanan, S., & Falk, T. H. (2019, July). Stress and anxiety measurement" in-the-wild" using quality-aware multi-scale hrv features. In 2019 41st Annual According to the International Conference of the IEEE), HRV was found to have a major correlation with factors measuring quality of life, such as mental and social job stressors, mental job stress and anxiety, and mental fatigue; and job stressors, anxiety, and mental fatigue were found to be related to work performance.

On the other hand, the mental state classification platform 120 may obtain a second numerical value indicating a possibility that the user corresponds to the mental state based on the extracted HRV variables (HRV data) by executing a second algorithm. In an embodiment, since the second numerical value is obtained from HRV data of the user while the questionnaire is performed, the second numerical value may be a numerical value associated with the reliability of the questionnaire.

FIG. 3 shows classification criteria graphs for classifying a plurality of mental states through HRV data of a mental state classification server according to an embodiment of the present disclosure.

Referring to FIG. 3, a step of performing the second algorithm executed by the mental state classification platform 120 may include classifying a severity of the mental state by applying a mental disorder screening model to the extracted HRV data to obtain a second numerical value. That is, the second numerical value may include the severity of the mental state.

For example, the mental state classification platform 120 may extract HRV variables (HRV data) such as HR value, LF value, and HF value by real-time image processing of the received face image, and then classify the mental state of the user by analyzing the extracted HR values, LF values, and HF values as cutoff criteria of the mental disorder screening model. Here, the HR value is related to depressive symptoms, the LF value is related to mental stress and fatigue, and the HF value may decrease when suffering from constant stress, fear, anxiety, or anxiety.

For example, as shown in FIG. 3 below, when the HR value is less than 65.3 to 76.3 in the major depressive disorder category, it may be classified as 'not depressed'; when the HR value is 76.3 to 82.3, it may be classified as 'intermediate'; and the HR value may be classified as 'serious' when it is greater than 82.3 to 93.1.

For example, as shown in FIG. 3, the anxiety disorder can be classified as 'not anxious' when the LF value is 5.63 to 5.71; and can be classified as 'serious' when the LF value is 5.39 to 5.51.

For example, as in FIG. 3, the adaptation disorder can be classified as 'not an adaptation disorder' when the HF value is 296.76 to 368.89; and can be classified as 'serious' when the HF value is 165.42 to 229.06.

For example, as in FIG. 3, the PTSD can be classified as 'not PTSD' when the HF value is 296.76 to 368.89; and can be classified as 'serious' when the HF value is 165.42 to 229.06.

For example, as in FIG. 3, the suicidal ideation can be classified as 'not at risk of suicide' when the HF value is less than 6.2 to 6.9; can be classified as 'mild' when the HF value is 5.5 to 6.2; and can be classified as 'serious' when the HF value is less than 5.2 to 5.5.

For example, as in FIG. 3, the insomnia can be classified as 'not insomnia' when the LF value is more than 7.11 to 8.14; can be classified as 'mild' when the LF value is 6.62 to 7.11; and can be classified as 'serious' when the LF value is less than 6.34 to 6.62.

In addition, the mental state classification platform 120 may execute a third algorithm to obtain the third numerical value indicating a possibility that the user corresponds to the mental state based on the first numerical value and the second numerical value. Here, the third numerical value may include a severity of the mental state. In an embodiment, the third algorithm may set weights for the first numerical value and the second numerical value; and obtain the third numerical value based thereon. For example, the mental state classification platform 120 may execute the third algorithm to reflect the mental state result classified according to the first numerical value as 95% in a final classification result, and the mental state classified according to the second numerical value by reflecting the result as 5% in the final classification result, to drive a third numerical value indicating the final classification result. In another embodiment, the mental state classification platform 120 may derive a third numerical value representing the final classification result by multiplying the first numerical value by a weight by the second numerical value by executing the third algorithm.

Figure 4:
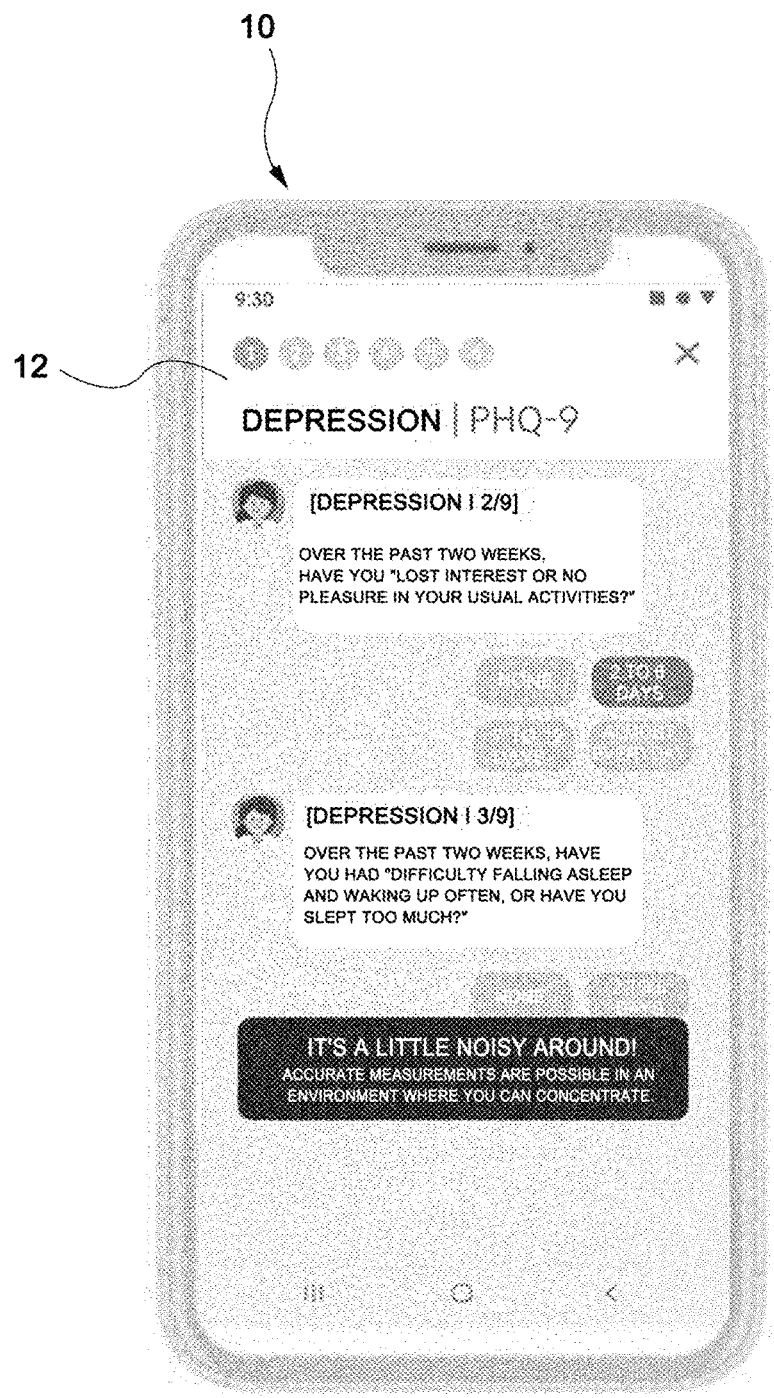
FIG. 4 is a schematic diagram illustrating a state of a receiving terminal to which a questionnaire of a mental state classification service is provided through a mental state classification server according to another embodiment of the present disclosure.

FIG. 4 is a schematic diagram illustrating a state of the receiving terminal 10 provided with a questionnaire of a mental state classification service through the mental state classification server 100 according to another embodiment of the present disclosure.

Referring to FIG. 4 together with FIG. 2, the terminal 10 according to another embodiment of the present disclosure may perform photographing of the user's face with the camera 14 in a background while inputting the answer to a questionnaire for classifying the at least one psychological state. Here, the background execution refers to executing the application program behind the user interface 12 invisible so as not to interfere with the user. For example, unlike the terminal 10 of FIG. 2, the terminal 10 of FIG. 4 may photograph the user's face with the camera 14 without displaying a camera photographing screen on the user interface 12.

Figure 5:
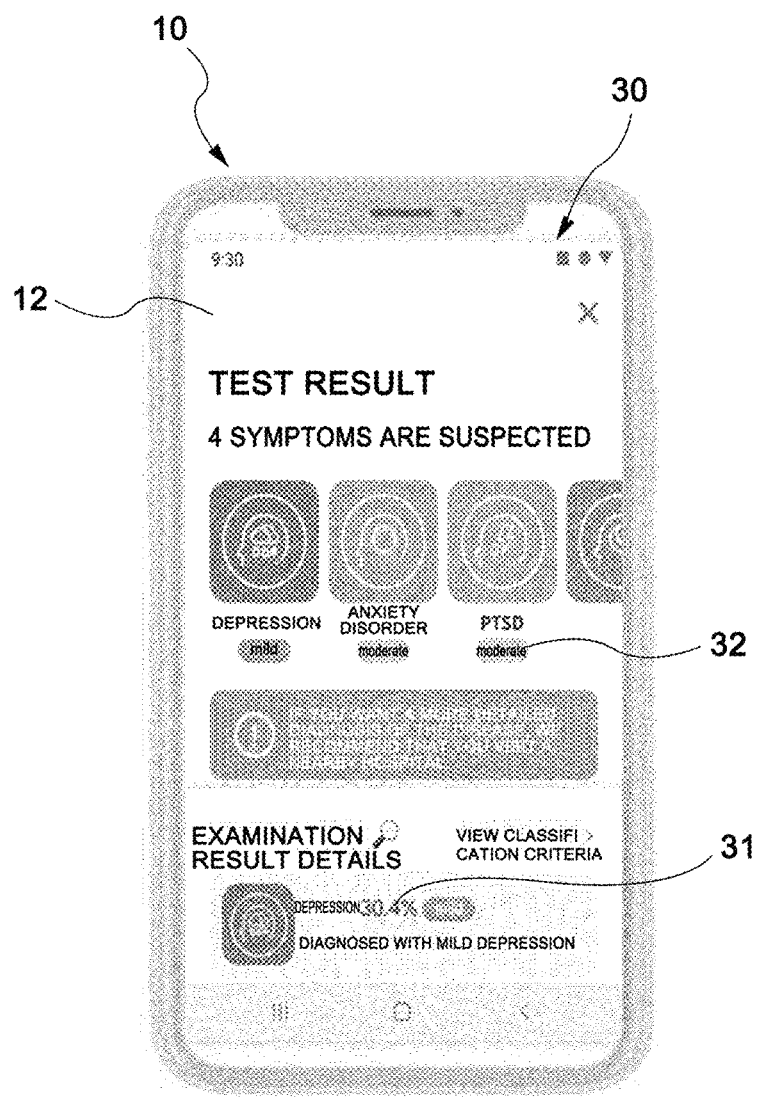
FIG. 5 is a diagram illustrating a state in which a mental state classification result report is provided to a terminal of the user by a mental state classification server according to an embodiment of the present disclosure.

FIG. 5 is a diagram illustrating a state in which a user's individual mental state classification result report 30 is provided to the user's terminal 20 by the mental state classification server 100 according to an embodiment of the present disclosure.

Referring to FIG. 5 together with FIG. 1, the mental state classification platform 120 may be configured to generate a mental state classification result report 30 indicating the mental state having the third numerical value. The mental state classification platform 120 may indicate a possibility that the user corresponds to at least one mental state in the mental state classification result report 30 as a percentage 31 and a plurality of stages 32. For example, the plurality of stages may be five levels of 'not', 'mild', 'moderate', 'moderately severe', and severe'; four levels of 'not', 'mild', 'moderate', and 'severe'; and three levels of 'not', 'moderate', and 'severe' and the like. This stage division is exemplary, and the stage division may be two stages or six stages or more.

For example, the major depressive disorder can be divided into five levels: not depressive, mild, moderate, moderately severe, and severe.

For example, the anxiety disorder can be divided into four levels: not anxious, mild, moderate, and severe.

For example, the adaptation disorder can be divided into two levels: not an adaptation disorder, and severe.

For example, the PTSD can be divided into three levels: non-PTSD, moderate, and severe.

For example, the insomnia may be divided into four levels: not insomnia, mild, moderately severe, and severe.

For example, the suicidal ideation may be divided into three levels of not suicidal ideation, mild, and severe.

It will be understood that the stage division for each of the above mental states is exemplary, and the stage division may be different according to settings.

Accordingly, the mental state classification server 100 according to an embodiment of the present disclosure may include the service platform 110 and the mental state classification platform 120; and may finally classify the user's mental state by considering both the result of classifying the mental state based on the answer to the questionnaire for classifying the mental state and the result of classifying the mental state based on the HRV data. Accordingly, the mental state classification server 100 of the present disclosure can effectively increase accuracy and reliability of the user's mental state classification.

Furthermore, the mental state classification server 100 of the present disclosure may extract the HRV data based on the user's answer to the questionnaire and the user's face image captured by the camera while the user inputs the answer to the questionnaire into the terminal 10; and thus it is possible to solve problems of the prior art that occur when the user does not answer accurately enough to indicate his/her actual mental state. That is, according to the mental state classification server 100 of the present disclosure, even if the user does not input an accurate answer to the questionnaire corresponding to the mental state, a more accurate mental state classification for a corresponding psychological state may be analyzed through a face image captured while inputting the answer to the questionnaire.

The service platform 110 may be configured to receive the mental state classification result report 30 from the mental state classification platform 120; and provide the mental state classification result report 30 to the user. For example, as shown in FIG. 5, the service platform 110 may transmit the mental state classification result report 30 to the terminal of the user through e-mail.

In addition, the mental state classification result report 30 may further include behavioral recommendations for the corresponding mental state in response to the third numerical value for the mental state being greater than or equal to a predetermined scale. For example, the mental state classification platform 120 may indicate the third numerical value in the mental state classification result report 30 by representing the user's mental state as three levels of mild, moderate, and severe.

In addition, the mental state classification platform 120 may include, in response to the mild mental state of the user, contents recommending self-regulation using a digital therapeutic agent in the mental state classification result report 30. The mental state classification platform 120 may include, in response to the user's moderate mental state, contents recommending self-regulation using the digital therapeutic agent and recommendation to visit a local hospital in the group's mental state classification result report 30. The mental state classification platform 120 may include, in response to the user's mental state being severe, contents recommending a visit to a university hospital in the mental state classification result report 30.

Figure 6A:
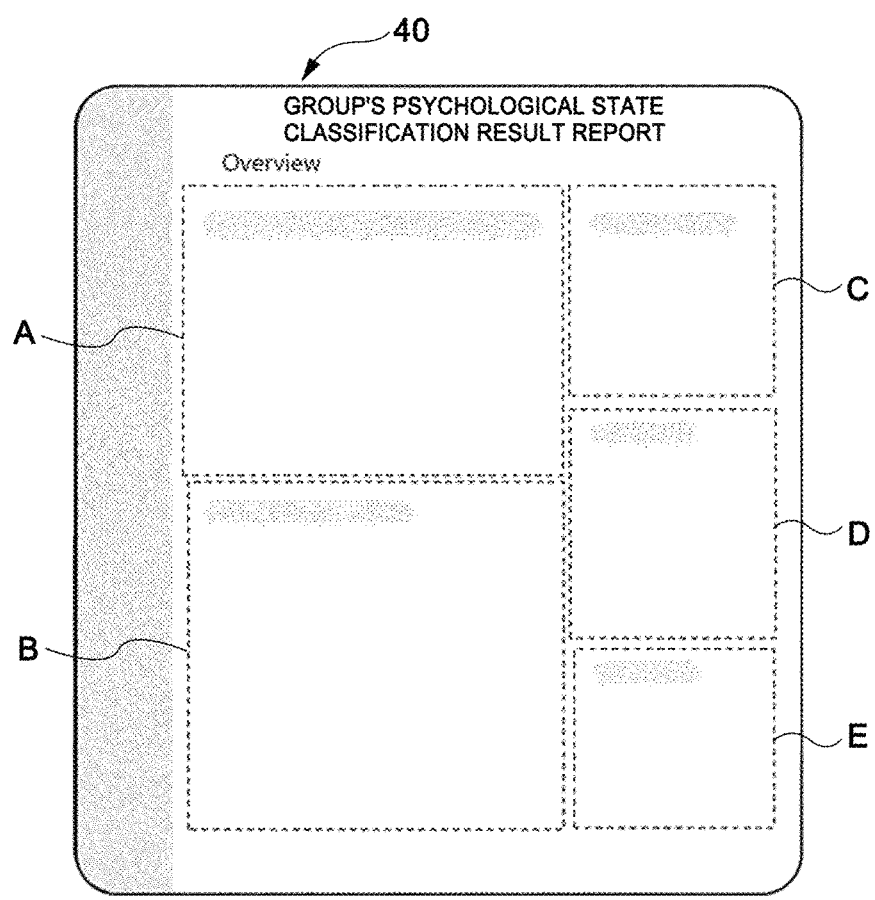
FIG. 6A is a diagram illustrating a state in which a group's mental state classification result report is provided to a terminal of an administrator by a mental state classification server according to an embodiment of the present disclosure.
Figure 6B:
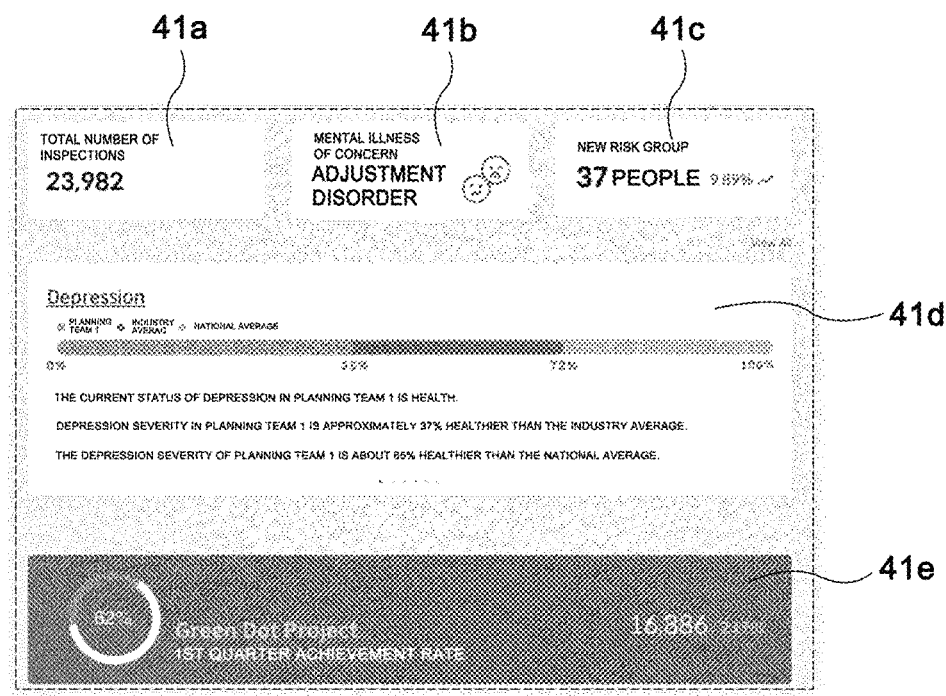
FIG. 6B is an enlarged view of region A of FIG. 6A of the present disclosure.
Figure 6C:
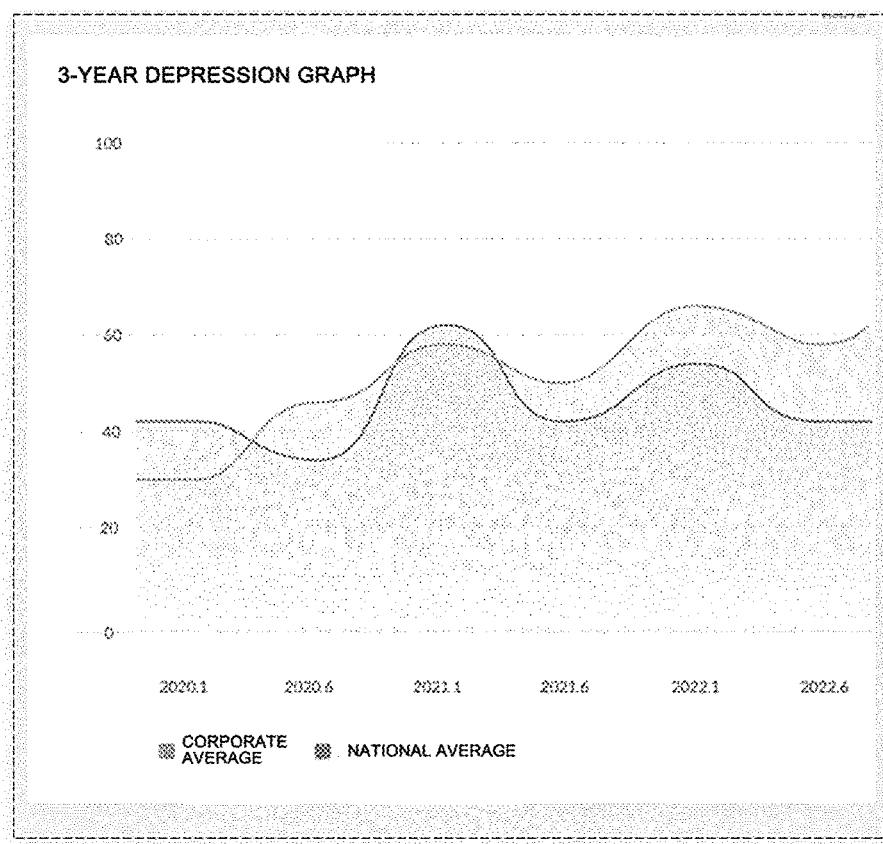
FIG. 6C is an enlarged view of region B of FIG. 6A of the present disclosure.
Figure 6D:
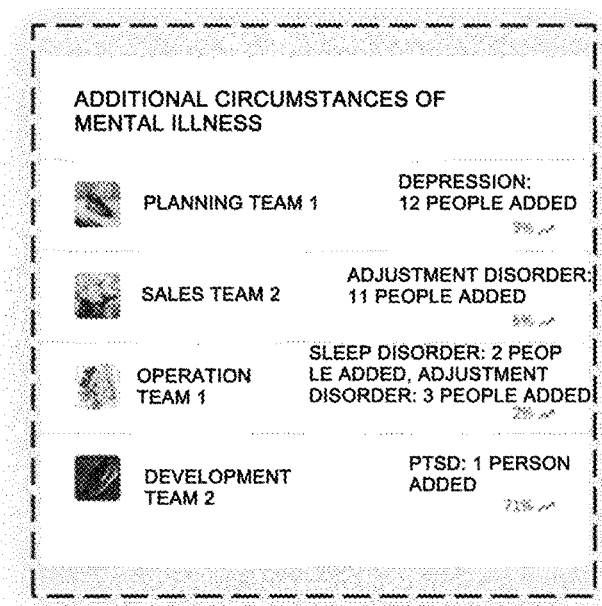
FIG. 6D is an enlarged view of region C of FIG. 6A of the present disclosure.
Figure 6E:
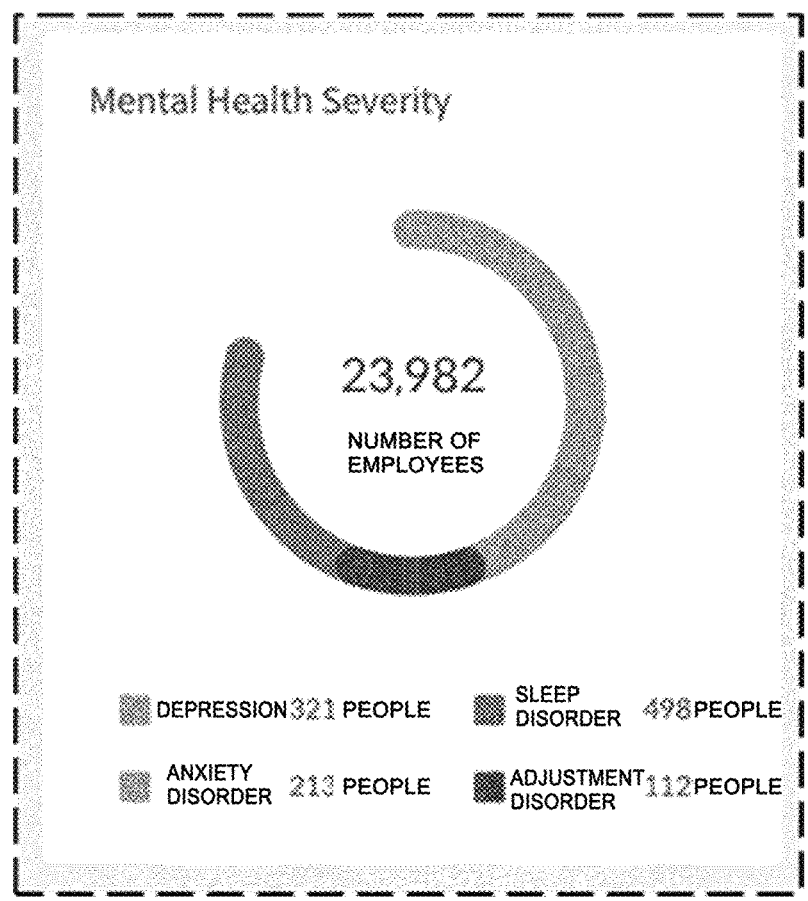
FIG. 6E is an enlarged view of region D of FIG. 6A of the present disclosure.
Figure 6F:
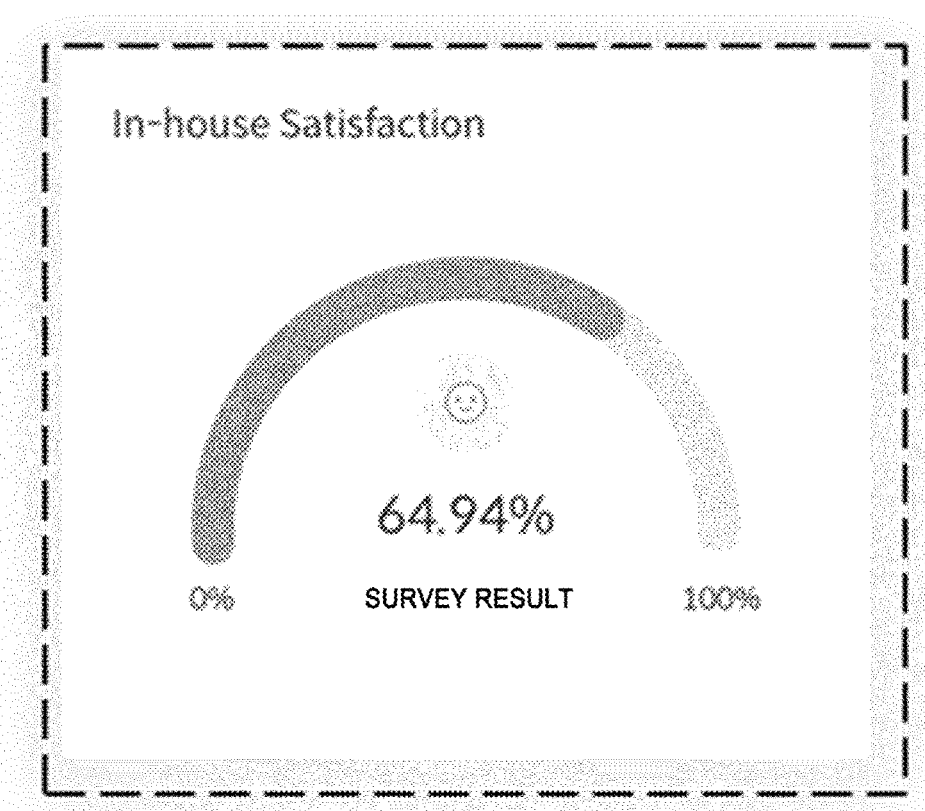
FIG. 6F is an enlarged view of region E of FIG. 6A of the present disclosure.

FIG. 6A is a diagram illustrating a state in which a group's mental state classification result report is provided to an administrator's terminal by a mental state classification server according to an embodiment of the present disclosure. FIG. 6B is an enlarged view of region A of FIG. 6A of the present disclosure. FIG. 6C is an enlarged view of region B of FIG. 6A of the present disclosure. FIG. 6D is an enlarged view of region C of FIG. 6A of the present disclosure. FIG. 6E is an enlarged view of region D of FIG. 6A of the present disclosure. FIG. 6F is an enlarged view of region E of FIG. 6A of the present disclosure.

Referring to FIGS. 6A to 6F together with FIG. 5, the mental state classification server 100 may perform the mental state classification of a plurality of users included in one group; and the mental state classification platform 120 may further generate a mental state classification result report 40 indicating an average of the third numerical value of the users included in the group derived from the third algorithm. That is, the mental state classification platform 120 may generate the group's mental state classification result report 40 so that only the average of the third value of the group is shown, and an individual third value of the members of the group is not included. Accordingly, the mental state classification server 100 of the present disclosure may not expose the user's mental state to the administrator, so that the user can honestly input an answer to the questionnaire.

The service platform 110 may be configured to receive the group's mental state classification result report 40 from the mental state classification platform 120, and provide the received group's mental state classification result report 40 to an administrator who manages the group.

As shown in FIGS. 6A to 6F, the service platform 110 may transmit the group's mental state classification result report 40 to the administrator through an application program of the terminal 10. For example, as shown in FIGS. 6A to 6F, the mental state classification platform 120 may generate the group's mental state classification result report 40 so that the group's mental state classification result is displayed as a percentage ratio and a graph, etc. based on the third numerical value of the group to which the user belongs.

The group's mental state classification result report 40 may be generated so that the classification result of the mental state of the group is displayed as a percentage ratio, a graph, or the like.

For example, as in FIG. 6B, the group's mental state classification result report 40 may include a total number of people tested 41a, a main mental state classification result 41b, an increase/decrease in the number of people in a specific psychological state 41c, a graph 41d showing a ratio of each level of depression in the group, and a graph 41e showing a ratio of achieving a health goal of mental state among group members.

For example, as shown in FIG. 6C, the group's mental state classification result report 40 may include a depression graph of a national average and a depression graph of the employee group of a corresponding company.

For example, as shown in FIG. 6D, the group's mental state classification result report 40 may represent an increase or decrease of a specific mental state (depression, adjustment disorder, sleep disorder, PTSD, etc.) of each team member of the company as the number of people.

For example, as shown in FIG. 6E, the group's mental state classification result report 40 may represent the mental state classification result of all employees of the company in a donut-type graph. Here, the donut-shaped graph may represent the ratio of the number of persons corresponding to each of depression, sleep disorder, anxiety disorder, and adjustment disorder, among the total number of people.

For example, as shown in FIG. 6F, the group's mental state classification result report 40 may represent a degree of satisfaction with the mental state classification service of the employee group of the corresponding company (in-house satisfaction) as a graph. Therefore, the service platform 110 may provide the group's mental state classification result report 40 to the administrator who manages the user group, so that the mental state classification server 100 of the present disclosure can help the administrator manage the mental state of the user group well.

The mental state classification platform 120 may improve the third algorithm through machine learning using artificial intelligence. In an embodiment, the mental state classification platform 120 may receive a result of classifying the at least one mental state of the user by a person. The mental state classification platform 120 may improve the third algorithm by performing machine learning of artificial intelligence based on the first numerical value, the second numerical value, the third numerical value, and the result classified by the person so that a fourth algorithm can be derived. That is, the mental state classification platform 120 may derive the fourth algorithm by adjusting the degree to which each of the first value and the second value is reflected in the third value so that the third value may be close to the result of a person (e.g., a specialist) directly classifying the user's mental state. In addition, the mental state classification platform 120 may be configured to replace (update) the third algorithm with the derived fourth algorithm.

Accordingly, the mental state classification server 100 of the present disclosure may provide a more accurate mental state classification service to the user by deriving the fourth algorithm in which the mental state classification platform 120 improves the third algorithm.

Figure 7:
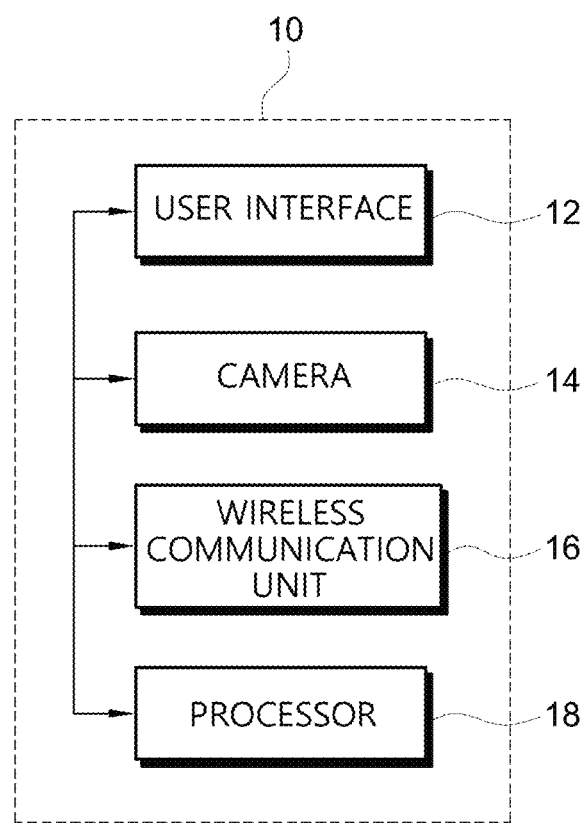
FIG. 7 is a conceptual diagram illustrating components of a terminal according to an embodiment of the present disclosure.

FIG. 7 is a conceptual diagram illustrating components of the terminal 10 according to an embodiment of the present disclosure.

Referring to FIG. 7, the terminal 10 configured to be accessible to the service platform 110 provided in the mental state classification server 100 according to an embodiment of the present disclosure is provided.

Specifically, the terminal 10 may include a user interface 12, a camera 14, a wireless communication unit 16, and a processor 18. The user interface 12 may display a questionnaire for classification of a mental state provided from the service platform 110. The user interface 12 may be configured so that a user of the terminal 10 may input an answer to the questionnaire. For example, when the terminal 10 is a smartphone, the user interface 12 may be a display capable of a touch input.

The camera 14 may be configured to generate a face image by photographing the face of the user of the terminal 10. That is, the camera 14 may be configured to capture an image of the user's face while the user inputs the answer to the questionnaire. For example, when the terminal 10 is a smartphone, the camera 14 of the smartphone may be a front camera 14 located at an upper end of the display unit of the smartphone.

The wireless communication unit 16 may be configured to receive the questionnaire from the service platform 110. The terminal 10 may receive the questionnaire information through Internet communication of the wireless communication unit 16. However, it is not necessarily limited to such Internet wireless communication, and the terminal 10 may receive the questionnaire contents through wired communication. The wireless communication unit 16 may be configured to transmit the answer input through the user interface 12 to the service platform 110 through Internet wireless communication. The wireless communication unit 16 may be configured to transmit the generated face image to the service platform 110 through Internet wireless communication.

The processor 18 manages and controls the components of the terminal 10. The processor 18 may be configured to control the user interface 12, the camera 14, and the wireless communication unit 16. For example, when the terminal 10 is a smartphone, the processor 18 may be an application processor (AP). In one embodiment, the processor 18 may be application specific integrated circuits (ASICs), digital signal processors (DSPs), digital signal processing devices (DSPDs), programmable logic devices (PLDs), field programmable gate arrays (FPGAs), controllers, micro-controllers, microprocessors, or any other type of processor or controller for performing other functions.

The processor 18 of the terminal 10 of the present disclosure may control the user interface 12 so that a virtual person transmits questions of the questionnaire to the user in the form of a chatting message, when providing the questionnaire to the user through the user interface 12. In an embodiment, the provision of the questionnaire may be performed by an application stored in the terminal 10.

The processor 18 may control the camera 14 to generate a face image by photographing the user's face whenever the user inputs an answer to the questionnaire through the user interface 12.

The processor 18 may control the wireless communication unit 16 to transmit the generated face image of the user to the service platform 110.

Since the user's face is photographed with the camera 14 while the user inputs the answer into the terminal 10, the terminal 10 of the present disclosure may provide the mental state classification server 100 with a face image captured while inputting the answer to the questionnaire so that the mental state classification server 100 can analyze a more accurate mental state classification for the corresponding mental state although the user does not input an accurate answer to the questionnaire corresponding to the mental state.

As shown in FIG. 2, the user may be configured to display at least a part of the user's face on the user interface 12 while the user inputs the answer to the questionnaire through the user interface 12 of the terminal 10. In this case, the face image being photographed through the camera 14 may be displayed at the top of the chatting (conversation) screen with a virtual person (agent) for mental state classification of the user interface 12. The face image may represent a middle of a forehead and both cheeks of the user's face. That is, a minimum camera view area to be displayed on the user interface 12 may correspond to the middle of the forehead and both cheeks of the face. In this regard, according to the objective self-awareness (OSA) theory and a method proven in OSA theory-related experiments, the minimum camera view area in which the user's face is captured is displayed on the user interface 12, so that the camera 14 can be used as a mirror and the user who recognizes his/her appearance may provoke self-reflection and enter a more truthful answer (Duval & Wicklund, 1972).

Accordingly, the terminal 10 of the present disclosure may display at least a part of the user's face on the user interface 12 of the terminal 10 while the camera 14 is photographing, thereby allowing the user to input the user's true answer to the questionnaire while the user inputs the answer to the questionnaire through the user interface 12 of the terminal 10.

Alternatively, as shown in FIG. 4, in the method of providing a mental state classification service of the present disclosure, during at least one questionnaire, the camera 14 may be executed in a background to prevent the user from recognizing the face photograph.

Figure 8:
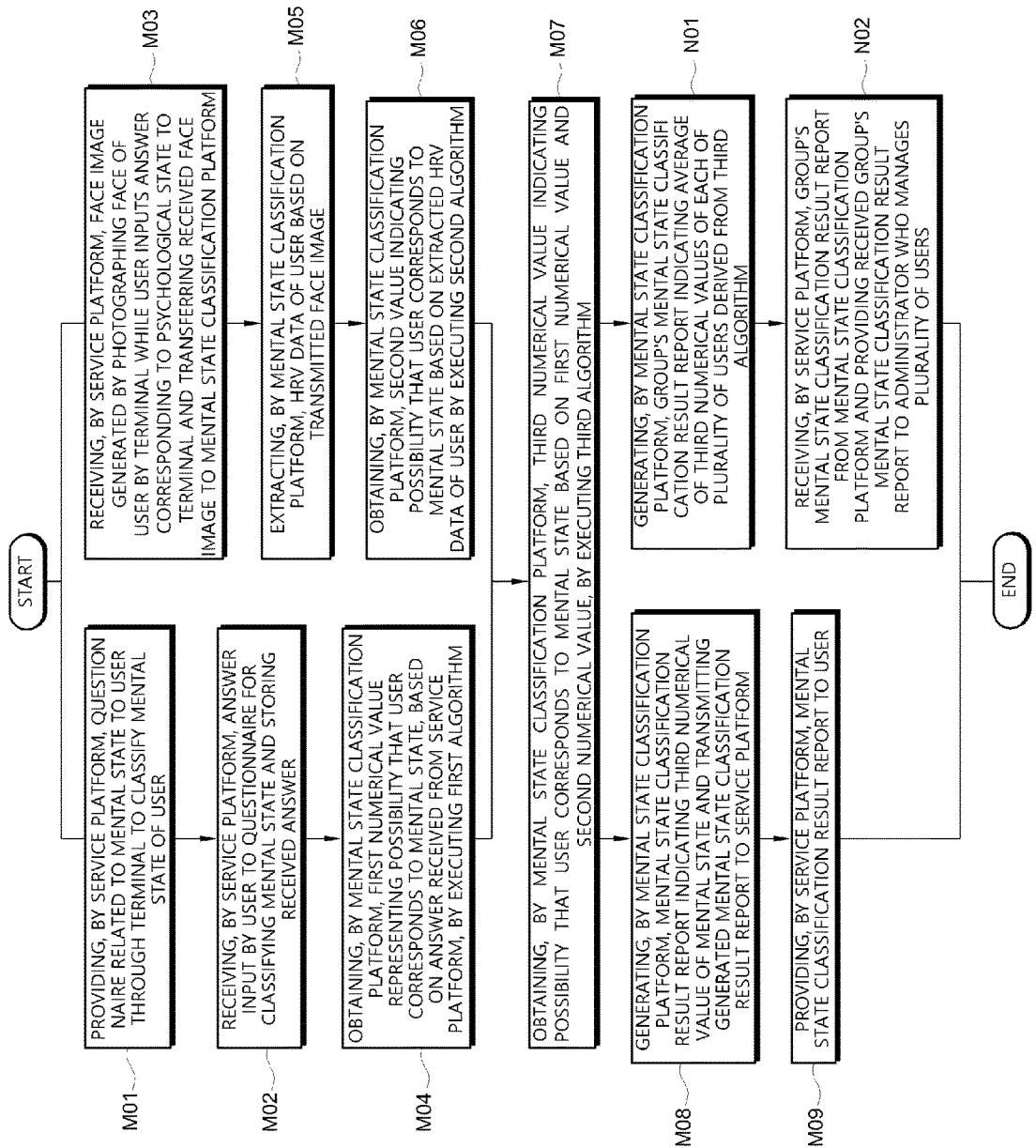
FIG. 8 is a flowchart illustrating a process of classifying a user's mental state in a method for classifying a mental state according to an embodiment of the present disclosure.

FIG. 8 is a flowchart illustrating a process of classifying a user's mental state in a method for classifying a mental state according to an embodiment of the present disclosure.

Referring to FIG. 8 together with FIG. 1, the mental state classification method according to an embodiment of the present disclosure is a method of classifying at least one mental state of a user of the terminal 10 using the mental state classification server 100 including the service platform 110 and the mental state classification platform 120.

Specifically, the mental state classification method may include a step M01 of providing, by the service platform 110, a questionnaire related to the mental state to the user through the terminal 10 to classify the mental state of the user.

The mental state classification method includes a step M02 of receiving, by the service platform 110, the answer input by the user to the questionnaire for classifying the mental state and storing the received answer.

The mental state classification method includes a step M03 of, by the service platform 110, receiving a face image generated by photographing the face of the user by the terminal 10 while the user inputs the answer corresponding to the psychological state to the terminal 10 and transferring the received face image to the mental state classification platform 120. Each questionnaire may include a plurality of questions.

The mental state classification method includes a step M04 of obtaining, by the mental state classification platform 120, a first numerical value representing a possibility that the user corresponds to the mental state, based on the answer received from the service platform 110, by executing a first algorithm.

The mental state classification method includes a step M05 of extracting, by the mental state classification platform 120, HRV data of the user based on the transmitted face image.

The mental state classification method includes a step M06 of obtaining, by the mental state classification platform 120, a second value indicating a possibility that the user corresponds to the mental state based on the extracted HRV data of the user by executing a second algorithm.

The mental state classification method includes a step M07 of obtaining, by the mental state classification platform 120, a third numerical value indicating a possibility that the user corresponds to the mental state based on the first numerical value and the second numerical value, by executing a third algorithm.

The mental state classification method includes a step M08 of generating, by the mental state classification platform 120, a mental state classification result report 30 indicating the third numerical value of the mental state and transmitting the generated mental state classification result report 30 to the service platform 110.

The mental state classification method includes a step M09 of providing, by the service platform 110, the mental state classification result report 40 to the user.

In this case, the service platform 110 may be configured to receive, in real time, a face image generated by photographing while the user inputs the answer corresponding to the mental state into the terminal 10. For example, the service platform 110 may receive, in real time, a face image generated by photographing a user's face while the user inputs answers to questionnaires corresponding to a plurality of mental states.

However, it is not necessarily limited to this form, and the mental state classification method may include classifying a plurality of mental states of the user, and, by the service platform, receiving a face image for each questionnaire section, generated by photographing the user's face image for each questionnaire section for each of the plurality of mental states. In addition, the mental state classification platform 120 may be configured to obtain a third numerical value for each questionnaire section based on the first value based on the answer to the questionnaire for each of the plurality of mental states and the second value based on the face image for each questionnaire section.

Therefore, the mental state classification method of the present disclosure may classify the mental state of the user by using the service platform 110 and the mental state classification platform 120 included in the mental state classification server 100, so that it is possible to finally classify the mental state of the user into a level indicating good or bad, considering both the mental state classification result based on the answers to the questionnaire for mental state classification and the mental state classification result based on the HRV data. Accordingly, the mental state classification method of the present disclosure can effectively increase accuracy and reliability of the user's mental state classification.

On the other hand, again referring to FIG. 8 together with FIGS. 1 and 6A, the mental state classification method may include: a step of N01 of generating, by the mental state classification platform 120, a group's mental state classification result report 40 indicating an average of the third numerical value of each of the plurality of users derived from the third algorithm; and a step of N02 of receiving, by the service platform 110, the group's mental state classification result report 40 from the mental state classification platform 120 and providing the received group's mental state classification result report 40 to an administrator who manages the plurality of users.

In addition, the step M08 may include a step (not shown) of adding an action recommendation for a mental state having the third numerical value to the mental state classification result report 30 in response to determining that the third numerical value is equal to or greater than the reference value. For example, the mental state classification platform 120 may represent the third numerical value as three levels of the user's mental state: mild, moderate, and severe. In addition, the step M08 may include: in response to the user's psychological state being mild, including in the psychological state classification result report 30 contents recommending self-regulation using a digital therapeutic agent; in response to the user's psychological state being moderate, including self-regulation using digital therapeutics and recommendations for visiting a local hospital in the psychological state classification result report 30; and in response to the user's psychological state being severe, including contents recommending a visit to a university hospital in the mental state classification result report 30.

Figure 9:
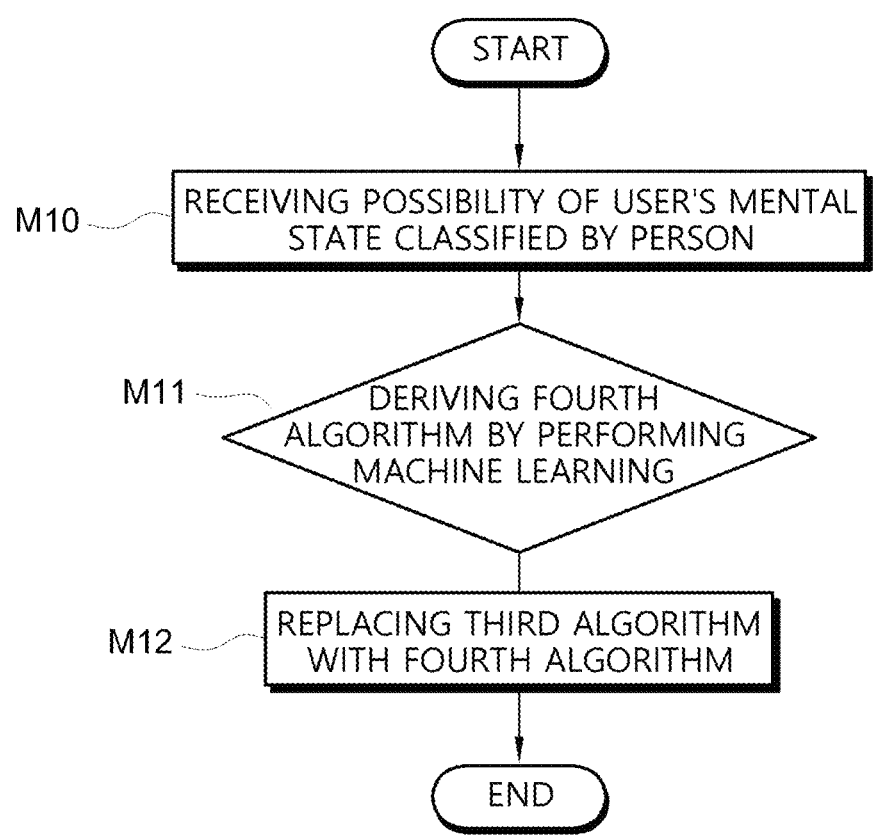
FIG. 9 is a flowchart illustrating a process of machine learning by a mental state classification platform of a mental state classification server according to an embodiment of the present disclosure.

FIG. 9 is a flowchart illustrating a process of machine learning by the mental state classification platform 120 of the mental state classification server 100 according to an embodiment of the present disclosure.

Referring to FIG. 9, the mental state classification method of the present disclosure, after the step M09 of providing the mental state classification result report 30 to the user, may further perform following steps M10, M11, and M12 for increasing accuracy of classifying the mental state of the user.

That is, the mental state classification method may further include: a step M10 of receiving, by the mental state classification platform 120, a possibility of the user's mental state classified by a person (e.g., a specialist); a step of M11 of deriving, by the mental state classification platform 120, a fourth algorithm that improves the third algorithm by performing machine learning of artificial intelligence based on the first numerical value, the second numerical value, the third numerical value, and the result classified by the person; and a step M12 of, by the mental state classification platform 120, replacing the third algorithm with the fourth algorithm.

Accordingly, the mental state classification method of the present disclosure may provide a more accurate mental state classification service to the user, by including the steps of, by the mental state classification platform 120, deriving the fourth algorithm that improved the third algorithm; and substituting the third algorithm for the derived fourth algorithm.

Figure 10:
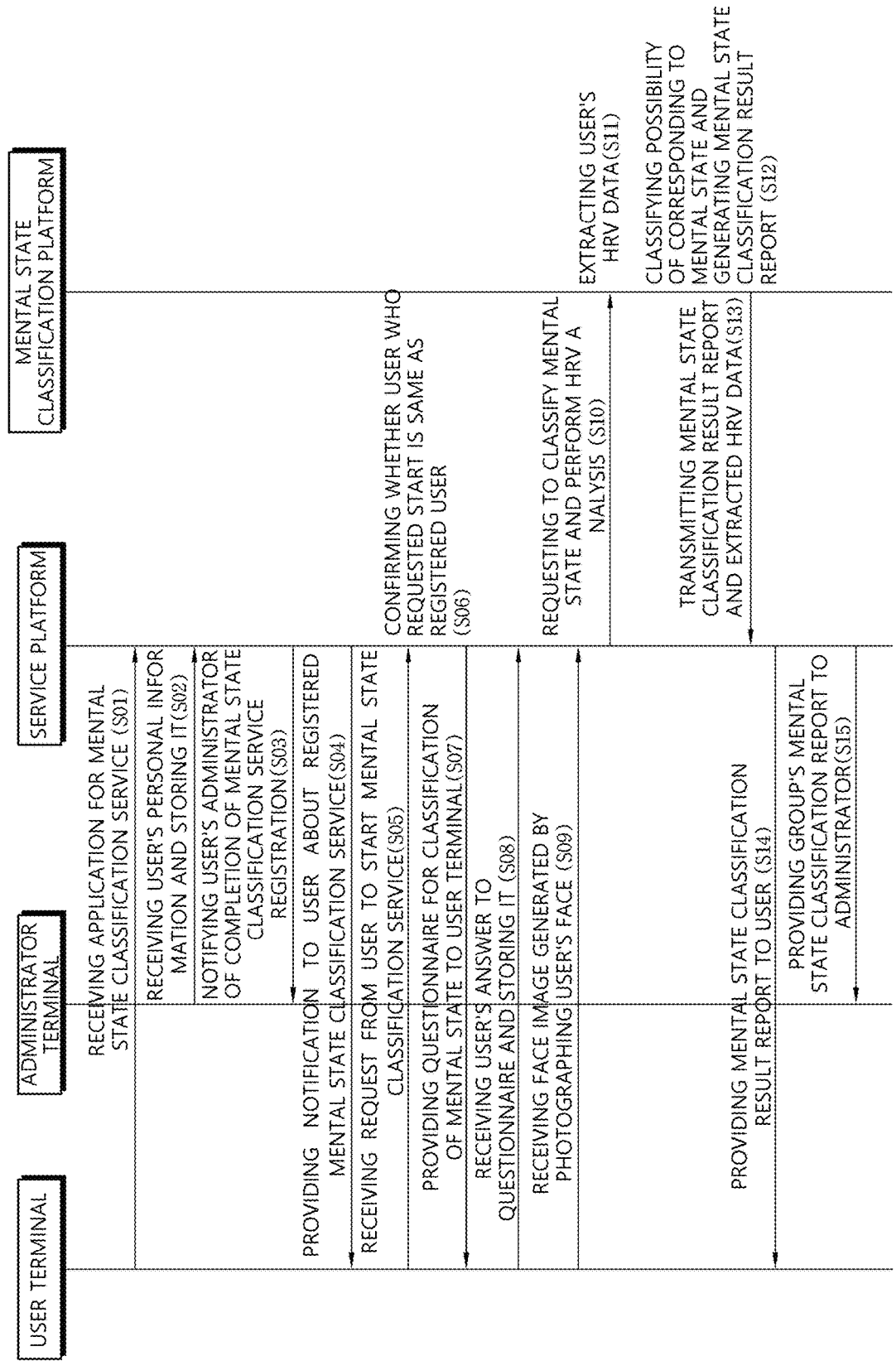
FIG. 10 is a flowchart illustrating steps of a method for providing a mental state classification service according to an embodiment of the present disclosure.

FIG. 10 is a flowchart illustrating steps of a method for providing a mental state classification service according to an embodiment of the present disclosure.

Referring to FIG. 10 together with FIGS. 1, 5, and 6A, a method of providing a mental state classification service according to an embodiment of the present disclosure is a method of providing a classification service of at least one mental state to a user using the mental state classification server 100, which includes the service platform 110 and the mental state classification platform 120.

Specifically, the method of providing the mental state classification service to the user may include a step S01 of receiving, by the service platform 110, an application for the mental state classification service from at least one of the user and the administrator who manages users. For example, the service platform 110 may start a mental state classification service in response to a request from the user or the administrator who wants to classify the mental state.

The method of providing the mental state classification service to the user may include a step S02 of receiving, by the service platform 110, the user's personal information and storing the personal information.

The method of providing the mental state classification service to the user may include a step S03 of notifying, by the service platform 110, the user's administrator of completion of the mental state classification service registration. The method of providing the mental state classification service to the user may further include a step S04 of providing, by the service platform 110, a notification to the user about the registered mental state classification service. The service platform 110 may check a HRV measurement environment through the user's terminal 10 after notifying the completion of the registration of the mental state classification service. For example, the method of checking the HRV measurement environment may check noise of the user's surrounding environment, brightness of lighting, an operating state of the camera 14, and the like.

The method of providing the mental state classification service to the user may include a step S05 of receiving, after providing the user with a registration notification of the mental state classification service, by the service platform 110, a request from the user to start the mental state classification service.

The method of providing the mental state classification service to the user may further include a step S06 of confirming, after receiving S05 the request to start the mental state classification service from the user, by the service platform 110, whether the user who requested the start of the mental state classification service is the same as the user registered in the service. In this case, the service platform 110 may check whether the user is the same person as the user registered in the service through a user authentication method. Here, the 'user authentication method' may be, for example, a method in which an authentication code is sent to the receiving terminal 10 as a text message, and the user of the receiving terminal 10 enters the authentication code at a user authentication site. In addition, the user authentication method may be a method of inputting first six digits of a resident number or transmitting the authentication code by e-mail.

The method of providing the mental state classification service to the user may include a step S07 of providing, by the service platform 110, a questionnaire for the classification of the mental state to the user's terminal 10.

The method of providing the mental state classification service to the user may include a step S08 of receiving, by the service platform 110, the user's answer to the questionnaire from the terminal 10 and storing the received answer.

The method of providing the mental state classification service to the user may include a step S09 of receiving, by the service platform, the face image generated by photographing the user's face while conducting the mental state questionnaire and the user's inputting the answer corresponding to the mental state into the terminal 10.

The method of providing the mental state classification service to the user may include a step S10 of transmitting, by the service platform 110, the answer to the user's questionnaire and the user's face image to the mental state classification platform 120 and requesting the mental state classification platform 120 to classify a mental state based on the transmitted user's answer and perform HRV analysis based on the transmitted face image.

The method of providing the mental state classification service to the user may include a step S11 of extracting, by the mental state classification platform 120, the user's HRV data based on the generated face image.

The method of providing the mental state classification service to the user may include a step S12 of classifying, by the mental state classification platform 120, a possibility of corresponding to the mental state based on the answer to the questionnaire and the extracted HRV data and generating the mental state classification result report 30 based on the classified result.

The method of providing the mental state classification service to the user may include a step S13 of transmitting, by the mental state classification platform 120, the mental state classification result report 30 and the extracted HRV data to the service platform 110.

The method of providing the mental state classification service to the user may include a step S14 of providing, by the service platform 110, the mental state classification result report 30 to the user.

Therefore, according to the method of providing the mental state classification service of the present disclosure, even if the user does not input an honest answer to the questionnaire corresponding to any one of the mental states, since it is possible to analyze a more accurate mental state classification for the mental state, a highly reliable mental state classification result report can be provided to the user.

According to one embodiment of the present disclosure, the method of providing a mental state classification service of the present disclosure may provide a classification service of a plurality of mental states of a user. In this case, the service platform 110 may receive an application about the classification service of the plurality of mental states of the user. The step S07 of, by the service platform 110, providing the questionnaire for classification of a mental state to the user's terminal, may include, by the service platform 110, providing a plurality of questionnaires for classification of a plurality of mental states to the user's terminal 10. The step S08 of, by the service platform 110, storing the answer may include, by the service platform 110, receiving the user's answers to each of the plurality of questionnaires and storing the received answers. The step S09 of receiving the face image may include, by the service platform 110, receiving a face image generated by photographing a face while the user inputs the answer to a questionnaire for each of the plurality of mental states. After the service platform 110 receives the face image, the method may further perform a step of, by the service platform 110, transmitting the face image to the mental state classification platform 120. In addition, the step S11 of extracting the HRV data may include a step of, by the mental state classification platform 120, extracting HRV data of the user that can classify each of the plurality of mental states based on all face images generated while inputting an answer to a questionnaire for each of the plurality of mental states.

According to another embodiment of the present disclosure, the method of providing a classification service of at least one mental state to the user may provide a classification service of a plurality of mental states of the user. Unlike the method of providing the mental state classification service of an embodiment of the present disclosure described above, the step S09 of receiving the face image may include a step of, by the service platform 110, receiving a face image generated by photographing a face for each section in which the user inputs the answer to the questionnaire for each of the plurality of psychological states and transmitting the face image to the mental state classification platform 120. In addition, the step S11 of extracting the HRV data may include a step of, by the mental state classification platform 120, extracting HRV data of the user that corresponds to each of the plurality of mental states based on the face image generated for each questionnaire section for each of the plurality of mental states.

In addition, as shown in FIG. 5, the generating of the mental state classification result report 30 may include, by the mental state classification platform 120, a possibility of corresponding to each of the mental states based on the answers to each of the plurality of questions and the extracted HRV data and generating the mental state classification result report 30 based on the classified result.

In another embodiment, the method of providing the mental state classification service may include, by the service platform 110, classifying the mental states of a plurality of users. The step S12 of generating the mental state classification result report 30 may include, by the mental state classification platform, further generating a group's mental state classification result report 40 representing an average of possibilities corresponding to the mental state of the plurality of users.

In another embodiment, the method may provide the mental state classification result report 30 of a plurality of users (i.e., a group) to the administrator. At this time, the step S13 may further include, by the service platform 110, receiving the group's mental state classification result report 40 from the mental state classification platform 120.

In addition, as shown in FIG. 6A, the method of providing a mental state classification service to the user may include a step S15 of receiving, by the service platform 110, the group's mental state classification report from the mental state classification platform 120 and providing the received group's mental state classification report to an administrator who manages the plurality of users.

The user's personal information may be at least one of a real name, gender, age (date of birth), a phone number, and work information (company name, affiliated department, affiliated team, job title, and number of years of service).

The at least one mental state may be a mental state related to a mental illness designated by the Korea Workers' Compensation and Welfare Service. For example, the at least one mental state may include major depression disorder, anxiety disorder, adjustment disorder, PTSD, suicidal ideation, and insomnia.

The step S07 of providing a questionnaire for classification of the user's mental state to the terminal 10 may include a step (not shown) of transmitting, through the user interface 12 of the terminal 10, the questionnaire to the user in a form of a chatting message by a virtual person. For example, as shown in FIG. 2, the service platform 110 may provide the questionnaire through an installed application program (e.g., an app) of the terminal 10. When the questionnaire is provided to the user, the virtual person may transmit the question of the questionnaire to the user in the form of a chatting message 2.

As shown in FIG. 2, the step S09 of, by the service platform 110, storing the user's face image photographed by the camera 14 of the terminal 10 may include displaying at least a part of the user's face, which is being photographed by the camera 14, while the user inputs the answer to the questionnaire through the user interface of the terminal 10. At this time, at least a part of the user's face being photographed by the camera 14 may be displayed on a top of the screen for a medical examination with a virtual person (i.e., agent) for mental state classification of the user interface 12.

In addition, at least a portion of the user's face may include a middle of a forehead and both cheeks of the user's face.

That is, according to the objective self-awareness (OSA) theory and the method proven in OSA theory-related experiments, the camera can be utilized as a mirror by displaying this minimum camera view on the user interface 12; so that a user who recognizes his/her appearance can provoke self-reflection and can enter a more truthful answer (Duval, S., & Wicklund, R. A. (1972). A theory of objective self awareness. New York: Academic Press.).

Accordingly, the method of providing the mental state classification service of the present disclosure includes the step of displaying at least a part of the user's face on the user interface 12 of the terminal 10 while the camera 14 is photographing, so that it is possible to induce the user to input a true answer to the questionnaire while the user is inputting the answer to the questionnaire through the user interface 12 of the terminal 10.

Figure 11:
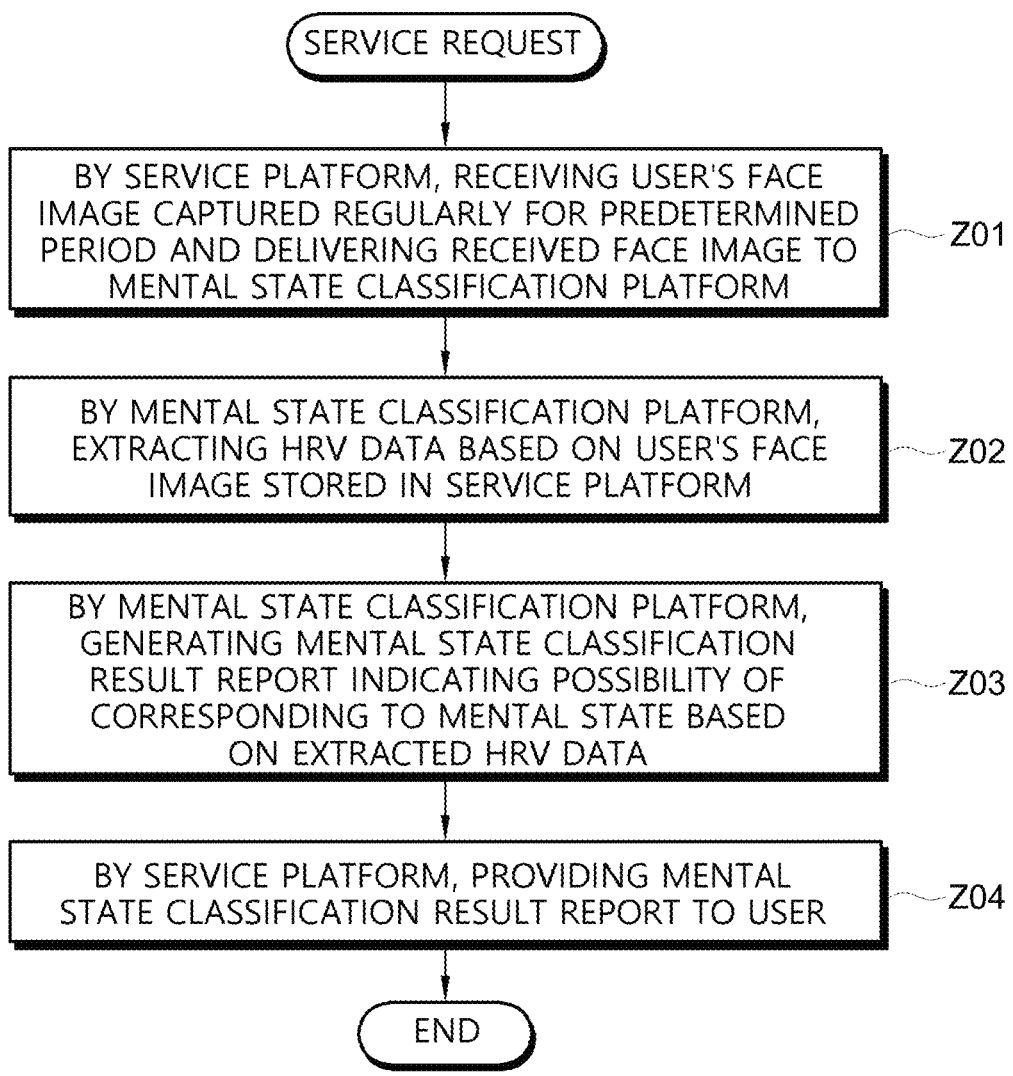
FIG. 11 is a flowchart illustrating steps of providing a mental state classification service in addition to the method of providing the mental state classification service according to an embodiment of the present disclosure.

FIG. 11 is a flowchart illustrating steps of providing a mental state classification service in addition to the method of providing the mental state classification service according to an embodiment of the present disclosure.

Referring to FIG. 11 together with FIG. 10, the method of providing a mental state classification service according to an embodiment of the present disclosure may further include: after the step S14 of providing the mental state classification result report to the user or the step S15 of providing the mental state classification result report to the administrator, a step Z01 of, by the service platform 110, receiving the user's face image captured regularly for a predetermined period and transmitting the received face image to the mental state classification platform 120; a step Z02 of, by the mental state classification platform 120, extracting HRV data based on the user's face image stored in the service platform 110; a step Z03 of, by the mental state classification platform 120, generating a mental state classification result report 30 indicating a possibility of corresponding to the mental state based on the extracted HRV data; and a step Z04 of, by the service platform 110, providing the mental state classification result report 30 to the user.

For example, the step Z01 may include a step of, by the service platform 110, receiving a face image generated by photographing the user's face once a week for four weeks from the terminal 10.

Therefore, the method of providing a mental state classification service according to an embodiment of the present disclosure can provide a regular mental state classification service to the user in a convenient way even after providing the mental state classification service to the user, so that it is possible to effectively help manage the user's mental health.

The apparatus and method described above may be implemented as a hardware component, a software component, and/or a combination of the hardware component and the software component. For example, devices and components described in the embodiments may be implemented using one or more general purpose computers or special purpose computers, for example, a processor, controller, arithmetic logic unit (ALU), digital signal processor, microcomputer, field programmable array (FPA), programmable logic unit (PLU), microprocessor, or a certain other device capable of executing and responding to instructions. The processing device may execute an operating system (OS) and one or more software applications running on the operating system. The processing device may also access, store, manipulate, process, and generate data in response to execution of the software. Although, for the convenience of understanding, there are instances where one processing device is described as being used, a person of ordinary skill in the art will recognize that a processing device may include a plurality of processing elements and/or a plurality of types of processing elements. For example, the processing device may include a plurality of processors or one processor and one controller. Other processing configurations are also possible, such as parallel processors.

Software may include a computer program, code, instructions, or a combination of one or more of these, and configure a processing unit to behave as desired, or independently or collectively give instructions to the processing unit. The software and/or data may be permanently or temporarily embodied on a certain machine, component, physical device, virtual equipment, computer storage medium or device, or transmitted signal wave in order to be interpreted by or to provide instructions or data to the processor. The software may be distributed over networked computer systems and stored or executed in a distributed manner. The software and data may be stored in one or more computer-readable recording media.

The described embodiments of the present disclosure also allow certain tasks to be performed on a distributing computing environment performed by remote processing devices that are linked through a communications network. In the distributed computing environment, program modules may be located in both local and remote memory storage devices.

As described above, although the embodiments have been described with reference to the limited drawings, those of ordinary skill in the art may apply various technical modifications and variations to the above, based on them. Appropriate results can be achieved when, for example, the described techniques are performed in an order different from the described method, and/or the described components of a system, structure, apparatus, circuit, etc. are combined or combined in a different form than the described method, or other components or an equivalent may be substituted or exchanged to achieve an appropriate result.

Therefore, other implementations, other embodiments, and equivalents to the claims are also within the scope of the following claims.

What is claimed is:

1. A server for classifying a plurality of mental states of a user, comprising:
   a service platform; and
   a mental state classification platform,
   wherein the service platform is configured to:
   provide a questionnaire corresponding to each of the plurality of mental states to a terminal of a user, and receive an answer of the user to the questionnaire from the terminal;
   receive a face image generated by photographing a face of the user while the user inputs the answer to the questionnaire for each of the plurality of mental states in the terminal of the user;
   enable the terminal to display the face image including at least a middle of a forehead and both cheeks of the face of the user on the user interface so that the user can recognize his/her appearance while inputting the answer to the questionnaire through the user interface of the terminal; and
   transmit the answer received from the user and the face image to the mental state classification platform,
   wherein the mental state classification platform is configured to:
   execute a first algorithm to obtain a first numerical value indicating a possibility that the user corresponds to each of the plurality of mental states based on the answer received from the terminal,
   extract heart rate variability (HRV) data of the user based on the face image received from the terminal;
   execute a second algorithm to obtain a second numerical value indicating a possibility that the user corresponds to each of the plurality of mental states based on the extracted HRV data;
   execute a third algorithm to obtain a third numerical value indicating a possibility that the user corresponds to each of the plurality of mental states based on the first numerical value and the second numerical value;
   and generate a mental state classification result report indicating the third numerical value,
   wherein each of the first numerical value and the second numerical value includes a severity of the mental state of the user, and
   wherein the third algorithm is configured to set a weight to be reflected in the third numerical value to each of the first numerical value and the second numerical value and obtain the third numerical value indicating a final mental state classification result from the first numerical value and the second numerical value based on the weight.

2. The server of claim 1, wherein the plurality of mental states are at least two of major depressive disorder, anxiety disorder, adjustment disorder, post-traumatic stress disorder (PTSD), suicidal ideation, and insomnia.

3. The server of claim 2, wherein the mental state classification platform is configured to receive the face image from the terminal in real time and extract the HRV data of the user in real time.

4. The server of claim 2, wherein the service platform is configured to provide the questionnaire for each of the plurality of mental states to the user, and receive in real time the face image for each questionnaire section, which is generated by photographing the face image of the user for each questionnaire section for each of the plurality of mental states, and
   wherein the mental state classification platform is configured to obtain the third numerical value for each of the plurality of mental states based on the first numerical value based on the answer to the questionnaire for each of the plurality of mental states and the second numerical value based on the entire face image generated for each questionnaire section of each of the plurality of mental states.

5. According to claim 1, wherein the service platform is configured to receive the mental state classification result report from the mental state classification platform and provide the mental state classification result report to the user.

6. The server of claim 5, wherein the mental state classification result report further comprises a behavioral recommendation for the mental state, in response to the third value for each of the plurality of mental states being greater than or equal to a selected first scale.

7. The server of claim 1, wherein the mental state classification server is configured to perform classification of each of the plurality of mental states of a plurality of users included in a specific group, and
   wherein the mental state classification platform is configured to further generate the mental state classification result report of the specific group including an average of the third numerical value of each of the plurality of users derived from the third algorithm and not including the third numerical value of each of the users, and wherein the service platform is configured to receive the mental state classification result report of the specific group from the mental state classification platform, and provide the received mental state classification result report of the specific group to an administrator who manages a plurality of users.

8. The server of claim 1, wherein the mental state classification platform is configured to:

receive a result of classifying the plurality of mental states of the user by a person;

derive a fourth algorithm that improves the third algorithm by performing machine learning of artificial intelligence based on the first numerical value, the second numerical value, the third numerical value, and the result classified by the person; and replace the third algorithm with the derived fourth algorithm.

9. A method of classifying a plurality of mental states of a user of a terminal using a mental state classification server including a service platform and a mental state classification platform, comprising:

by the service platform, providing a questionnaire related to each of the plurality of mental states to the user through the terminal to classify the plurality of mental states;

by the service platform, receiving the answer input by the user to the questionnaire and storing the received answer;

by the service platform, receiving a face image generated by photographing a face of the user while conducting the questionnaire for each of the plurality of mental states and the user's inputting the answer corresponding to each of the plurality of mental states into the terminal, and transmitting the received face image to the mental state classification platform;

by the mental state classification platform, obtaining a first value indicating a possibility that the user corresponds to each of the plurality of mental states based on the received answer by executing a first algorithm;

by the mental state classification platform, extracting heart rate variability (HRV) data of the user based on the transmitted face image;

by the mental state classification platform, obtaining a second value indicating a possibility that the user corresponds to each of the plurality of mental states based on the extracted HRV data of the user by executing a second algorithm;

by the mental state classification platform, executing a third algorithm, and obtaining a third numerical value indicating a possibility that the user corresponds to each of the plurality of mental states based on the first numerical value and the second numerical value;

by the mental state classification platform, generating a mental state classification result report indicating the third numerical value of each of the plurality of mental states, and transmitting the generated mental state classification result report to the service platform; and by the service platform, providing the mental state classification result report to the user, wherein the terminal is configured to display a face image including at least a middle of a forehead and both cheeks of the face of the user on a user interface so that the user can recognize his/her appearance while inputting the answer to the questionnaire through the user interface of the terminal, wherein each of the first numerical value and the second numerical value includes a severity of the mental state of the user, and wherein the third algorithm is configured to set a weight to be reflected in the third numerical value to each of the first numerical value and the second numerical value and obtain the third numerical value indicating a final mental state classification result from the first numerical value and the second numerical value based on the weight.

10. The method of claim 9, wherein the method comprises classifying each of the plurality of mental states of a plurality of users, and further comprising:

by the mental state classification platform, generating a group's mental state classification result report indicating an average of the third numerical value of each of the plurality of users derived from the third algorithm; and by the service platform, receiving the group's mental state classification result report from the mental state classification platform, and providing the group's received mental state classification result report to an administrator who manages the plurality of users.

11. The method of claim 9, wherein the generating a mental state classification result report indicating the third numerical value comprising:

in response to the mental state classification platform determining that the third numerical value is greater than or equal to a reference value, adding an action recommendation for the mental state having the third numerical value.

12. The method of claim 9, further comprising:

by the mental state classification platform, receiving a result of classifying the plurality of mental states of the user by a person;

by the mental state classification platform, deriving a fourth algorithm that improves the third algorithm by performing machine learning of artificial intelligence based on the first numerical value, the second numerical value, the third numerical value, and the result classified by the person; and by the mental state classification platform, replacing the third algorithm with the derived fourth algorithm.

13. A method of providing a classification service of a plurality of mental states to a user using a mental state classification server including a service platform and a mental state classification platform, comprising:

by the service platform, receiving an application for a mental state classification service from at least one of the user and an administrator who manages users;

by the service platform, receiving personal information of the user and storing the personal information;

by the service platform, notifying completion of registration of mental state classification service to at least one of the user and the administrator of the user;

by the service platform, providing a questionnaire for classification of each of the plurality of mental states to a terminal of the user;

by the service platform, receiving an answer of the user to the questionnaire from the terminal and storing the received answer;

by the service platform, receiving a face image generated by photographing a face of the user while conducting the questionnaire for each of the plurality of mental states and the user's inputting the answer corresponding to each of the plurality of mental states into the terminal;

by the service platform, transmitting the answer of the user to the questionnaire and the received face image to the mental state classification platform, and requesting the mental state classification platform to classify each of the plurality of mental states based on the transmitted answer of the user and perform HRV analysis based on the transmitted face image;

by the mental state classification platform, extracting HRV data of the user based on the face image;

by the mental state classification platform, classifying a possibility of corresponding to each of the plurality of mental states based on the answer to the questionnaire and the extracted HRV data, and generating a mental state classification result report based on classified results;

by the mental state classification platform, transmitting the mental state classification result report to the service platform; and by the service platform, providing the mental state classification result report to the user, wherein the receiving a face image generated by photographing a face of the user comprising:

displaying a face image including at least a middle of a forehead and both cheeks of the face of the user on a user interface of the terminal so that the user can recognize his/her appearance while inputting the answer to the questionnaire through the user interface.

14. The method of claim 13, wherein the receiving a face image generated by photographing a face of the user comprising:

by the service platform, receiving a face image generated by photographing a face for each section in which the user inputs the answer to the questionnaire for each of the plurality of mental states, and transmitting the face image to the mental state classification platform, and wherein the extracting HRV data of the user comprising:

by the mental state classification platform, extracting HRV data of the user corresponding to each of the plurality of mental states based on each face image generated for each questionnaire section for each of the plurality of mental states.

15. The method of claim 13, the method comprises classifying each of the plurality of mental states of a plurality of users, and further comprising:

by the mental state classification platform, further generating a group's mental state classification result report indicating an average of possibilities corresponding to each of the plurality of mental states of the plurality of users; and by the service platform, receiving the group's mental state classification result report from the mental state classification platform, and providing the received group's mental state classification result report to an administrator who manages the plurality of users.

16. The method of claim 13, wherein the plurality of mental states are at least two of major depressive disorder, anxiety disorder, adjustment disorder, PTSD, suicidal ideation, and insomnia.

17. The method of claim 13, wherein the providing a questionnaire for classification of each of the plurality of mental states to a terminal comprises:

transmitting the questionnaire to the user in a form of a chatting message by a virtual person in the user interface of the terminal.

18. The method of claim 13, after the providing the mental state classification result report to the user, further comprising:

by the service platform, receiving the face image of the user regularly photographed for a predetermined period, and transmitting the received face image to the mental state classification platform;

by the mental state classification platform, extracting HRV data based on the user's face image;

by the mental state classification platform, generating a mental state classification result report indicating a possibility of corresponding to each of the plurality of mental states based on the extracted HRV data; and by the service platform, providing the mental state classification result report to the user.

* * * * *